(12) United States Patent
Kinsho et al.

(10) Patent No.: US 11,629,119 B2
(45) Date of Patent: Apr. 18, 2023

(54) PROCESS FOR PREPARING 2-METHYL-N-(2'-METHYLBUTYL)BUTANAMIDE

(71) Applicant: Shin-Etsu Chemical Co., Ltd., Tokyo (JP)

(72) Inventors: Takeshi Kinsho, Joetsu (JP); Yusuke Nagae, Joetsu (JP); Shogo Tsukaguchi, Joetsu (JP); Yasuhiko Kutsuwada, Joetsu (JP); Tatsuya Hojo, Joetsu (JP); Takeru Watanabe, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 17/751,974

(22) Filed: May 24, 2022

(65) Prior Publication Data

US 2022/0411363 A1 Dec. 29, 2022

(30) Foreign Application Priority Data

Jun. 7, 2021 (JP) .............................. JP2021-095181

(51) Int. Cl.
  *C07C 231/14* (2006.01)
  *C07C 231/20* (2006.01)

(52) U.S. Cl.
  CPC .......... *C07C 231/14* (2013.01); *C07C 231/20* (2013.01)

(58) Field of Classification Search
  None
  See application file for complete search history.

(56) References Cited

U.S. PATENT DOCUMENTS

2020/0079799 A1   3/2020  Negishi et al.

FOREIGN PATENT DOCUMENTS

| AU | 4315596 A | 7/1996 |
| BR | 102017000486 A2 | 7/2018 |
| WO | 9619919 A1 | 7/1996 |

OTHER PUBLICATIONS

Leal et al. "Female sex pheromone of the longhorn beetle *Migdolus fryanus* Westwood: N-(2'S)-methylbutanoyl 2-methylbutylamine" Experientia, 50:853-856 (1994).
Santangelo et al. "Synthesis of the four possible stereoisomers of N-2'-methylbutyl-2-Methylbutylamide, the sex pheromone of the longhorn beetle *Migdolus fryanus* westwood" Synthetic Communications, 31(23):3685-3698 (2001).
Santangelo, Ellen M. "Stereoselective Syntheses of Semiochemicals—Applications in Ecological Chemistry" Doctoral Thesis, KTH Chemistry, Organic Chemistry, Stockholm, Sweden (60 pages) (2004).
Extended European Search Report corresponding to European Patent Application No. 22176459.0 (8 pages) (dated Nov. 2, 2022).
Lamb et al. "Borrowing hydrogen methodology for the conversion of alcohols into N-protected primary amines and in situ deprotection" Tetrahedron Letters, 50:3374-3377 (2009).

*Primary Examiner* — Sudhakar Katakam
*Assistant Examiner* — Jennifer C Sawyer
(74) *Attorney, Agent, or Firm* — Myers Bigel, P.A.

(57) ABSTRACT

The present invention provides a process for preparing 2-methyl-N-(2'-methylbutyl) butanamide of the following formula (1):the process comprising: subjecting an α-arylethyl-2-methylbutylamine compound of the following general formula (2): wherein Ar represents a substituted or unsubstituted aryl group having 6 to 20 carbon atoms, to N-2-methylbutyrylation to form an N-α-arylethyl-2-methyl-N-(2'-methylbutyl)butanamide compound of the following general formula (3): wherein Ar is as defined above, and removing the α-arylethyl group of the resulting compound (3) to form 2-methyl-N-(2'-methylbutyl)butanamide (1).

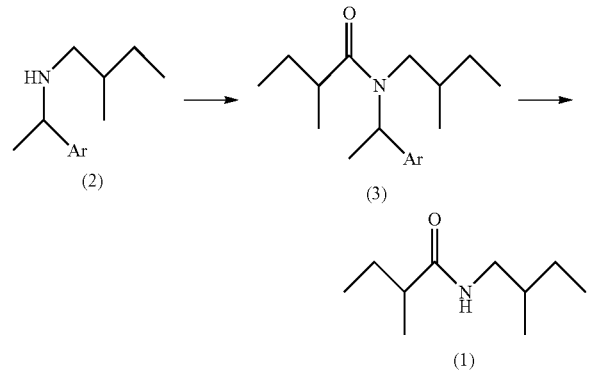

12 Claims, No Drawings

PROCESS FOR PREPARING 2-METHYL-N-(2'-METHYLBUTYL)BUTANAMIDE

TECHNICAL FIELD

The present invention relates to a process for preparing an amide compound, specifically 2-methyl-N-(2'-methylbutyl) butanamide.

BACKGROUND ART

Insect sex pheromones are biologically active substances which are usually borne by females to attract males, and exhibit a high attracting activity in a small amount. Sex pheromones are widely utilized as a means for forecasting outbreaks of pests and/or confirming geographic spread (invasion into a specific area), and also as a means for controlling pests. Widely used methods for controlling pests include a mass trapping method, a lure & kill or attract & kill method, a lure & infect or attract & infect method, and a mating disruption method. Before practical use of a sex pheromone, it is required to economically produce a sufficient amount of a sex pheromone for basic research and also for applications.

*Migdolus fryanus* (hereinafter abbreviated as "MFLB"), a species of the longhorn beetle belonging to the order *Coleoptera* and the family *Cerambycidae*, is an economically serious pest that mainly spreads in South America and seriously damages sugarcane.

A sex pheromone of MFLB has been identified as 2-methyl-N-(2'-methylbutyl)butanamide by Leal et al. (Non-Patent Literature 1 listed below) (the nomenclature of this compound will be described below). A natural product and a mixture of two synthetic diastereomers of this sex pheromone were analyzed by chiral phase gas chromatography, and the results showed that the asymmetric carbon atom (at position 2; the position number will be described below) in the acid moiety had an S absolute configuration. Although the absolute configuration of the asymmetric carbon atom (at position 2'; the position number will be described below) in the amine moiety failed to be analytically identified, it is expected to be S, based on biosynthetic reasoning, and the natural product is estimated to be a (2S,2'S)-isomer. Both the (2S,2'S)-isomer and the (2S,2'R/S)-isomer exhibited attracting activity in field tests of attraction (Non-Patent Literature 1 and Patent Literature 1 listed below).

Processes for preparing a sex pheromone of MFLB are reported, including a process for preparing four possible diastereomers described by Santangelo et al. (Non-Patent Literature 2 listed below) and a preparation process described by A.E.G. Santana et al. (Patent Literature 2 listed below).

In the prior literatures, different nomenclature and/or carbon numbering systems are used even for the same compound. Therefore, the nomenclature and carbon numbering system as used herein will be described in advance.

Inconsistent nomenclature for the pheromone compound of MFLB of the following formula (1):

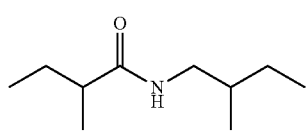
(1)

2-Methyl-N-(2'-methylbutyl)butanamide is used in the prior literatures. The pheromone compound is named N-2'-methylbutanoyl 2-methylbutylamine in Non-Patent Literature 1 and N-2'-methyl-2-methylbutylamide in Non-Patent Literature 2. This compound is an N-alkyl-substituted carboxamide and should be named on the base of an amide, which is a carboxylic acid derivative, as a parent name. The alkyl group on the nitrogen atom of this compound should be considered an alkyl substituent on the nitrogen atom of an amide rather than an amine. Therefore, this compound is named 2-methyl-N-(2'-methylbutyl)butanamide in the present specification. Also in the prior literatures, carbon atoms composing the acyl group in the carboxylate moiety are numbered 1', 2', 3', and 4' to indicate the position of methyl substitution, and carbon atoms composing the alkyl group on the nitrogen atom are numbered 1, 2, 3, and 4. In the present specification, a carbon chain considered as a parent chain in the nomenclature, that is, a carbon chain of the acyl moiety, is taken as a main chain, and the carbon chain of the alkyl moiety is taken as a side chain. When it is required to specify on which of the carbon chains a carbon atom of interest is present, carbon atoms composing the main chain are numbered 1, 2, 3, and 4, and carbon atoms composing the side chain are numbered 1', 2', 3', and 4'. This numbering system is different from those used in Non-Patent Literatures 1 and 2. It should be noted that the structural formula in Scheme 3 shown in page 3689 of Non-Patent Literature 2 has incorrect stereochemical designation.

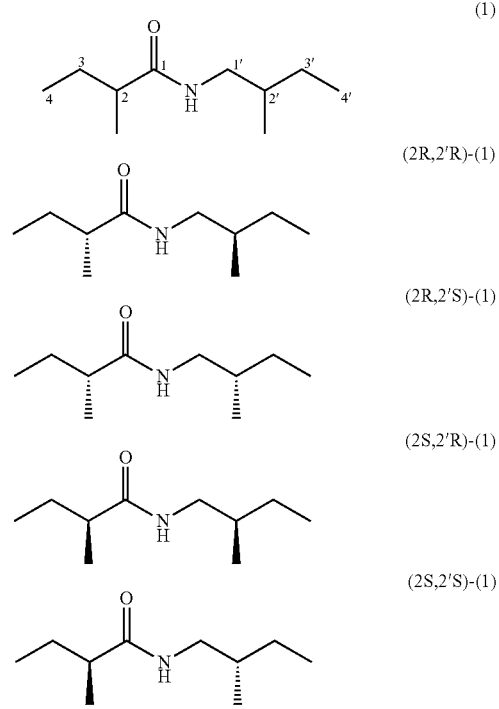

wherein the wedged bonds represent an absolute configuration.

LIST OF THE LITERATURES

[Patent Literatures]
[Patent Literature 1] WO96/19919, corresponding to AU4315596

[Patent Literature 2] Brazil Patent Application Publication No. 102017000486 [Non-Patent Literatures]
[Non-Patent Literature 1] W.S. Leal et al., Experientia, 50, 853 (1994)
[Non-Patent Literature 2] E.M. Santangelo et al., Synthetic Communications, 31, 3685 (2001)

PROBLEMS TO BE SOLVED BY THE INVENTION

To establish techniques for controlling pests utilizing the sex pheromone MFLB, it is required to economically produce a sufficient amount of the sex pheromone for basic researches, applied research, and/or practical uses. For example, it is desirable in basic researches to determine whether the naturally produced MFLB pheromone is a single stereoisomer (2S,2'S)-isomer (or possible (2S,2'R)-isomer) identified in Non-Patent Literature 1 or a mixture of these isomers. For comparative studies of the activities of four possible diastereomers, it is desirable to selectively synthesize each stereoisomer in a high optical purity. On the other hand, the pheromone to be used in large amounts for applications and/or practical use, for instance for forecasting outbreak of pests and/or controlling pests, is not necessarily a pure stereoisomer, and a mixture of stereoisomers that has activity as attractants or mating disruptants may be economically more advantageous. A mixture of stereoisomers to be used may be a mixture containing the natural isomer or a mixture containing unnatural isomers only. The mixture containing the natural isomer is thought to be more preferable in view of the activity.

For such purposes, there has been a high demand for a process applicable to both basic researches and applications for efficiently preparing the pheromone compound of MFLB in an industrially practical scale.

In the processes described in both Non-Patent Literature 2 and Patent Literature 2, 2-methylbutylamine is subjected to butyrylation with a 2-methylbutanoic acid derivative to form the target compound.

In the process described in Patent Literature 2, the 2-methylbutanoic acid derivative is 2-methylbutyryl chloride (2-methylbutanoyl chloride).

2-Methylbutylamine is commercially available, but is expensive and difficult to obtain in bulk. Particularly its optically active (S)-isomer is commercially available, but its (R)-isomer is difficult to obtain. Therefore, in Non-Patent Literature 2, (R)-2-methylbutylamine is obtained, starting from methyl (S)-(+)-3-hydroxy-2-methylpropionate via an (R)-2-methylbutanol derivative in multistep conversion.

In addition, 2-methylbutylamine is highly volatile and is, therefore, difficult to handle (e.g., to be concentrated and then isolated in a liquid state). Moreover, 2-methylbutylamine has disadvantages such as bad odor.

Furthermore, in Non-Patent Literature 2, the optical purity of optically active 2-methylbutylamine was determined by converting 2-methylbutylamine into a corresponding MTPA amide derivative and analyzing the derivative. However, the $^1$H-and $^{19}$F-NMR spectral signals were insufficiently separated, and the peak separation in chiral phase gas chromatography and/or chiral phase high performance liquid chromatography was impossible, leading to unsuccessful determination of correct optical purity.

Although the starting material was optically pure, the $^1$H-NMR spectrum of 2-methylbutylamine MTPA amide with the insufficient peak separation showed the optical purity of "at least 65%". This suggests that racemization occurred probably in the step of producing the intermediate, 2-methylbutyryl chloride. Here, Non-Patent Literature 2 states "epimerization", however, 2-methylbutylamine has a single asymmetric carbon atom, so that "racemization" is correct. The intermediate 2-methylbutyryl chloride, which was used in the final step in Patent Literature 2 and Non-Patent Literature 2, results in the decreased optical purity of the target optically active amide compound. This means that the acylation with the intermediate 2-methylbutyryl chloride is inappropriate.

Thus, the known preparation processes have many problems, and there has been a great need for a process that overcomes these problems and prepares efficiently and industrially practically 2-methyl-N-(2'-methylbutyl)butanamide.

SUMMARY OF THE INVENTION

The present invention has been made in these circumstances, and aims to provide a process for preparing efficiently and industrially practically the pheromone of MFLB, 2-methyl-N-(2'-methylbutyl)butanamide.

The present inventors have contemplated a plan for synthesis of the target compound (1) as shown below:

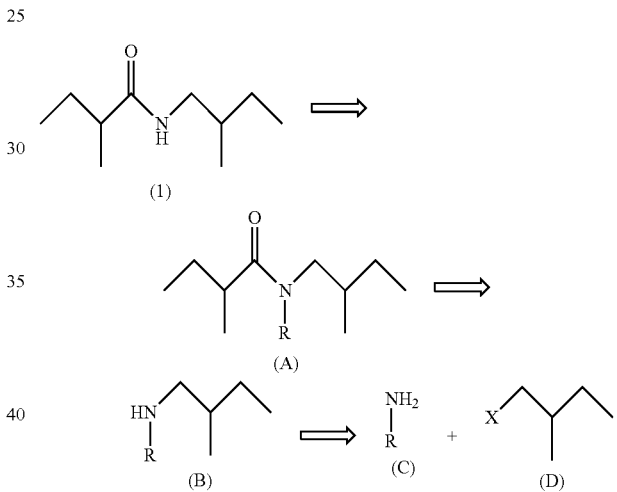

wherein the open arrows represent transforms in the retrosynthetic analysis, R represents a protecting group, and X represents a leaving group.

A protected amine compound (B) is assumed as a key synthesis intermediate. A target amide compound (1) may be prepared by subjecting the compound (B) to N-2-methylbutyrylation to form a protected amide compound (A) and removing the protecting group R in the protected amide compound. The protected amine compound (B) may be prepared by subjecting an amine compound (C) to N-methylbutylation with a methylbutylating agent (D) having a leaving group X which is to be substituted with a nucleophile in nucleophilic substitution, rather than by introducing a protecting group into 2-methylbutylamine. This step allows one to avoid direct use of 2-methylbutylamine which is difficult to obtain and handle. Here, the group R is not a protecting group in a strict sense, because this is not a case where a functional NH group of an amine compound is protected with a protecting group, followed by some conversion and removal of the protecting group to regenerate the functional NH group. However, for convenience, the group R is referred to as "a protecting group", and the removal thereof is referred to as "removal of the protecting group" herein. Examples of the 2-methylbutylating agent (D) include those having various leaving groups X that can be N-alkylated, specifically 2-methylbutyl halides (having a leaving group X that represents a halo group (halogen atom)), 2-methylbutyl sulfonates (having a leaving group X that represents a sulfonate group), and/or 2-methylbutyl phosphonates (having a leaving group X that represents a phosphonate group). Starting materials for the 2-methylbutylating agent (D) include inexpensive 2-methylbutanol (having X that represents a hydroxyl group) whose (±)-form and optically active form are both available.

As the result of the researches with the consideration of these circumstances, the present inventors have found that an α-arylethyl group is useful as a protecting group R to prepare a stereoisomer (enantiomer or diastereomer) of the target compound and a mixture thereof, and thus have completed the present invention.

In an aspect of the present invention, the present invention provides [1] a process for preparing 2-methyl-N-(2'-methylbutyl)butanamide of the following formula (1):

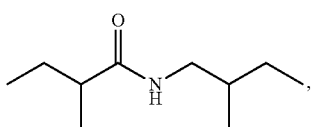
(1)

the process comprising:

subjecting an α-arylethyl-2-methylbutylamine compound of the following general formula (2):

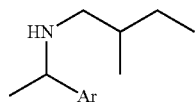
(2)

wherein Ar represents a substituted or unsubstituted aryl group having 6 to 20 carbon atoms, to N-2-methylbutyrylation to form an N-α-arylethyl-2-methyl-N-(2'-methylbutyl)butanamide compound of the following general formula (3):

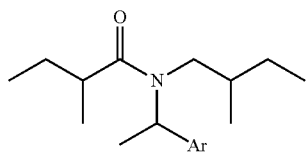
(3)

wherein Ar is as defined above, and removing the α-arylethyl group of the resulting compound (3) to form 2-methyl-N-(2'-methylbutyl)butanamide (1).

In another aspect of the present invention, the present invention provides [2] the process for preparing 2-methyl-N-(2'-methylbutyl)butanamide according to [1], the process further comprising:

subjecting an α-arylethylamine compound of the following general formula (4):

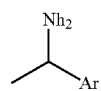
(4)

wherein Ar is as defined above, to N-2-methylbutylation to form the α-arylethyl-2-methylbutylamine compound (2).

In another aspect of the present invention, the present invention provides [3] the process for preparing 2-methyl-N-(2'-methylbutyl)butanamide according to [1], wherein the N-α-arylethyl-2-methyl-N-(2'-methylbutyl)butanamide compound (3) is a (2S)-N-α-arylethyl-2-methyl-N-(2'-methylbutyl)butanamide compound of the following general formula (2S)-(3):

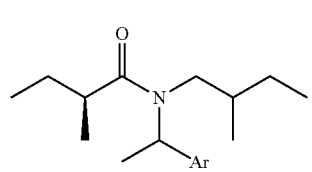
(2S)-(3)

wherein the wedged bond represents an absolute configuration, and Ar is as defined above, and wherein the 2-methyl-N-(2'-methylbutyl)butanamide (1) is (2S)-2-methyl-N-(2'-methylbutyl)butanamide of the following general formula (2S)-(1):

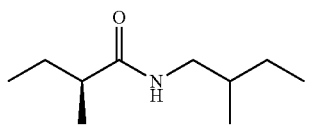
(2S)-(1)

wherein the wedged bond is as defined above.

In another aspect of the present invention, the present invention provides [4] the process for preparing 2-methyl-N-(2'-methylbutyl)butanamide (1) according to [2], wherein the α-arylethyl-2-methylbutylamine compound (2) is a (2S)-α-arylethyl-2-methylbutylamine compound of the following general formula (2S)-(2):

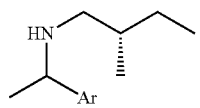
(2S)-(2)

wherein the wedged bond and Ar are as defined above, wherein the N-α-arylethyl-2-methyl-N-(2'-methylbutyl)butanamide compound (3) is a (2'S)-N-α-arylethyl-2-methyl-N-(2'-methylbutyl)butanamide compound of the following general formula (2'S)-(3):

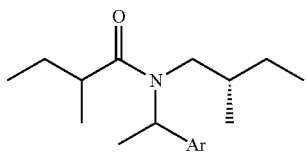

(2'S)-(3)

wherein the wedged bond and Ar are as defined above, and wherein 2-methyl-N-(2'-methylbutyl)butanamide (1) is (2'S)-2-methyl-N-(2'-methylbutyl)butanamide of the following formula (2'S)-(1):

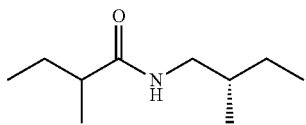

(2'S)-(1)

wherein the wedged bond is as defined above.

In another aspect of the present invention, the present invention provides [5] the process for preparing 2-methyl-N-(2'-methylbutyl)butanamide (1) according to [2] or [4], wherein the α-arylethyl-2-methylbutylamine compound (2) is a (2S)-α-arylethyl-2-methylbutylamine compound of the following general formula (2S)-(2):

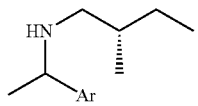

(2S)-(2)

wherein the wedged bond represents an absolute configuration, and Ar is as defined above, wherein the N-α-arylethyl-2-methyl-N-(2'-methylbutyl)butanamide compound (3) is a (2S,2'S)-N-α-arylethyl-2-methyl-N-(2'-methylbutyl)butanamide compound of the following general formula (2S,2'S)-(3):

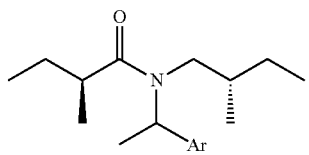

(2S,2'S)-(1)

wherein the wedged bonds and Ar are as defined above, and wherein 2-methyl-N-(2'-methylbutyl)butanamide (1) is (2S,2'S)-2-methyl-N-(2'-methylbutyl)butanamide of the following formula (2S,2'S)-(1):

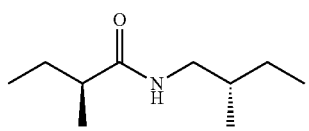

(2S,2'S)-(1)

wherein the wedged bonds are as defined above.

In another aspect of the present invention, the present invention provides [6] the process for preparing 2-methyl-N-(2'-methylbutyl)butanamide (1) according to any of [1] to [5], the process further comprising, prior to the N-2-methylbutyrylation, isolating a mixture of diastereomers of an α-arylethylamine compound of the following general formulae (2R*,αR*)-(2) and (2S*,αR*)-(2):

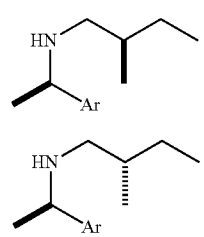

(2R*,αR*)-(2)

(2S*,αR*)-(2)

wherein the hashed bond and the bold bonds represent a relative configuration, and Ar is as defined above, from the α-arylethyl-2-methylbutylamine compound (2), and subjecting at least one of the α-arylethylamine compounds (2R*,αR*)-(2) and (2S*,αR*)-(2) isolated from the mixture of diastereomers to N-2-methylbutyrylation and d the removal of the α-arylethyl group.

In one aspect of the present invention, the present invention provides [7] a process for preparing a mixture of diastereomers of the following general formulae (2R*,αR*)-(2) and (2S*,αR*)-(2) of an α-arylethylamine compound:

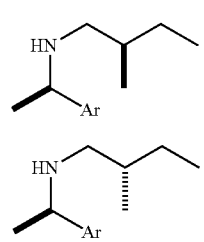

(2R*,αR*)-(2)

(2S*,αR*)-(2)

wherein the hashed bond and the bold bonds represent a relative configuration, and Ar represents a substituted or unsubstituted aryl group having 6 to 20 carbon atoms, the process comprising:

separating a mixture of the diastereomers (2R*,αR*)-(2) and (2S*,αR*)-(2) of the α-arylethylamine compound from the α-arylethyl-2-methylbutylamine compound (2).

According to the present invention, it is possible to prepare efficiently and industrially practically 2-methyl-N-(2'-methylbutyl)butanamide.

DETAILED DESCRIPTION OF THE PREFERRED EMBODIMENTS

Embodiments of the present invention will be described in detail below. It should be noted that the present invention is not limited to or by the embodiments.

The intermediates, the reagents, and the target compounds represented by the chemical formulae in the present specification may sometimes comprise stereoisomers such as enantiomers or diastereomers. Unless otherwise stated, the chemical formulae shall be interpreted to represent all of these isomers. The isomers may be used alone or in combination at any ratio. A 50:50 mixture of two enantiomers is a racemic mixture, and a mixture containing two enantiomers at a non-equivalent ratio is a scalemic mixture. Either a racemic mixture or a scalemic mixture may be used.

Stereochemical notation in the present specification follows the IUPAC Recommendations 2006; Pure Appl. Chem., 78, 1897, (2006).

For example, the following formula without specific stereochemical notation:

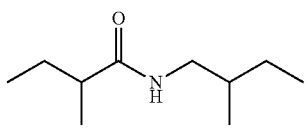

represents any ones of the following possible enantiomers and diastereomers, mixtures of any combinations thereof at any ratio, or a mixture of all of these isomers at any ratio:

(2R,2'R)-Isomer

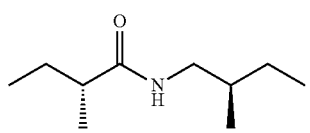

(2R,2'S)-Isomer

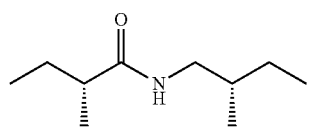

(2S,2'R)-Isomer

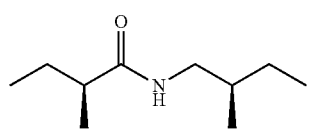

(2S,2'S)-Isomer

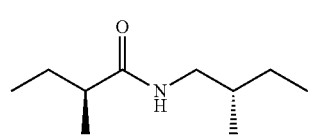

wherein the bold wedged bonds and the hashed wedge bonds represent an absolute configuration.

The following formula with specific stereochemical notation:

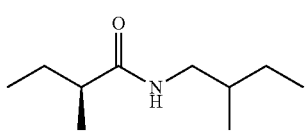

represents any ones of diastereomers with the specified S configuration at position 2, or a mixture thereof at any ratio:

(2S,2'R)-Isomer

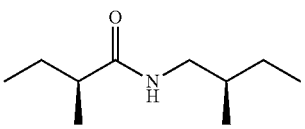

(2S,2'S)-Isomer

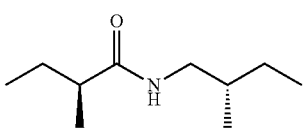

wherein the bold wedged bonds and the hashed wedge bond are as defined above.

The following formula with specific stereochemical notation:

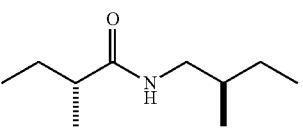

wherein the bold bond and the hashed bond represent a relative configuration represents any ones of the following enantiomers with the determined absolute configuration or a mixture thereof at any ratio:

(2R,2'R)-Isomer

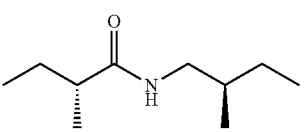

(2S,2'S)-Isomer

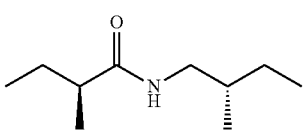

wherein the bold wedged bonds and the hashed wedge bonds are as defined above.

For a compound having a carbon chain of an acyl moiety and a carbon chain of an alkyl moiety, to indicate a carbon atom having a methyl substituent or the like, carbon atoms composing the carbon chain of the acyl moiety, which is considered as a parent chain in the nomenclature and is taken as a main chain, are numbered 1, 2, 3, and 4, and carbon atoms composing the carbon chain of the alkyl moiety, which is taken as a side chain, are numbered 1', 2', 3', and 4' to indicate the position of alkyl substitution. Positions of carbon atoms having an α-arylethyl moiety in a synthesis intermediate having an α-arylethyl group are indicated by α and β.

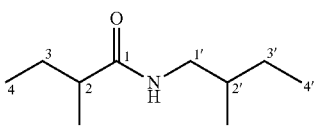

-continued

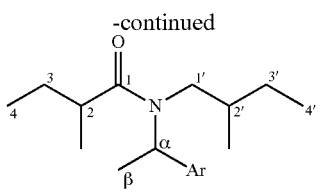

Embodiments of the present invention will be described by step in detail below.

Step of subjecting an α-arylethylamine compound to N-2-methylbutylation

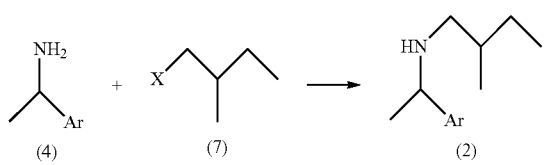

wherein Ar represents a substituted or unsubstituted aryl group having 6 to 20 carbon atoms, and X represents a leaving group.

An α-arylethylamine compound (4) is subjected to N-2-methylbutylation with a 2-methylbutylating agent (7) to form an α-arylethyl-2-methylbutylamine compound (2), which is a key intermediate of the present invention.

Ar in the α-arylethylamine compound (4) is a substituted or unsubstituted aryl group having 6 to 20 carbon atoms.

Examples of the unsubstituted aryl group include an aryl group in which any one of hydrogen atoms of aromatic hydrocarbon compounds having 6 to 20 carbon atoms or their hydrogenated derivatives is substituted with a bond. Examples of the aromatic hydrocarbon compounds include benzene, naphthalene, anthracene, phenanthrene, tetracene, indene, azulene, biphenylene, indacene, acenaphthylene, fluorene, phenalene, fluoranthene, pyrene, indane, and tetralin.

Examples of the substituted aryl groups include aryl groups in which one or more hydrogen atoms at any position of the unsubstituted aryl groups are substituted with a halo group, a nitro group, and a hydrocarbon group such as a methyl group or an ethyl group. Preferred examples of the substituted or unsubstituted aryl groups include a phenyl group, a tolyl group, a naphthyl group, a phenanthryl group, and these groups substituted with a halo group or a methyl group. Particularly preferred examples include a phenyl group, a tolyl group (including an o-tolyl group, an m-tolyl group, and a p-tolyl group), a xylyl group (including those having any substitution position), a 1-naphthyl group, a 2-naphthyl group, and these groups substituted with a halo group or a nitro group, in view of the price of starting materials and/or reagents, the industrial availability, and/or the ease of resolution of diastereomers in the case where a specific stereoisomer is synthesized by separating the diastereomer as an intermediate as described below. The α-arylethylamine compound (4) may be its (±)-form or its optically active (R)- or (S)- form having any optical purity. Particular preferred examples of the optically active substances used include (R)-α-phenylethylamine or (S)-α-phenylethylamine and (R)-α-1-naphthylethylamine or (S)-α-1-naphthylethylamine in view of the industrial availability. Advantages of using the optically pure α-arylethylamine compound (4) will be described below.

The leaving group X in the 2-methylbutylating agent (7) may be selected from any leaving groups that are known to allow N-alkylation to proceed. Examples of the leaving group X include, but are not particularly limited to, a halo group, an alkanesulfonyloxy group, an arenesulfonyloxy group, a dialkylphosphoryloxy group, and a diarylphosphoryloxy group. Preferred specific examples include halo groups such as a chloro group, a bromo group, and an iodo group; alkanesulfonyloxy groups such as a methanesulfonyloxy group and a trifluoromethanesulfonyloxy group; arenesulfonyloxy groups such as a benzenesulfonyloxy group and a p-toluenesulfonyloxy group; and phosphoryl groups such as a dimethylphosphoryl group and a diphenylphosphoryl group, in view of the price of starting materials and/or reagents and the industrial availability.

Particularly preferred specific examples of the 2-methylbutylating agent (7) include 1-chloro-2-methylbutane, 1-bromo-2-methylbutane, 1-iodo-2-methylbutane, 2-methylbutyl methansulfonate, and 2-methylbutyl p-toluenesulfonate. The 2-methylbutylating agent (7) may be its (±)-form or its optically active (R)- or (S)-form having any optical purity.

The 2-methylbutylating agent (7) may be prepared from a corresponding alcohol, 2-methylbutanol, for example, in a conventional method. The starting material 2-methylbutanol may be its (±)-form or its optically active (R)- or (S)-form having any optical purity to prepare an optically active 2-methylbutylating agent (7). Capability to use optically active 2-methylbutanol as a starting material in the preparation process of the present invention without using optically active 2-methylbutylamine, is a great advantage of the preparation process of the present invention in the light of the expensiveness and industrial unavailability of optical active 2-methylbutylamine. The 2-methylbutylating agent (7) may be commercially available one or may be prepared in house. In the latter case, the 2-methylbutylating agent (7) may be prepared in advance or may be prepared in situ.

The N-2-methylbutylation reaction is allowed to proceed b typically adding sequentially or simultaneously the α-arylethylamine compound (4) and the 2-methylbutylating agent (7) in the presence of a base in a solvent or without a solvent, with heating or cooling.

An amount of the α-arylethylamine compound (4) used may be optionally chosen and is typically from 0.02 to 500 mol, preferably from 0.2 to 50 mol, more preferably from 0.9 to 5 mol, per mol of the 2-methylbutylating agent (7). When the unreacted α-arylethylamine compound (4) can be recovered, the α-arylethylamine compound (4) is preferably used in excess relative to the 2-methylbutylating agent (7) to completely consume the 2-methylbutylating agent (7), in view of the yield and/or efficiency.

The base used in the N-2-methylbutylation reaction is an inorganic base or an organic base.

Example of the inorganic base include hydroxides such as sodium hydroxide, potassium hydroxide, lithium hydroxide, and barium hydroxide; carbonate salts such as sodium carbonate, potassium carbonate, lithium carbonate, barium carbonate, sodium bicarbonate, and potassium bicarbonate; hydride salts such as sodium hydride and lithium hydride; ammonia; and urea.

Example of the organic base include a primary, secondary, or tertiary alkylamine, arylamine, and alkylarylamine and a nitrogen-containing aromatic compound. When a primary amine or a secondary amine is used as a base, the base competes for N-2-methylbutylation with the α-arylethylamine compound (4). Therefore, a tertiary amine is preferably used. The tertiary amine is preferably triethylamine, tri-n- butylamine, diethylisopropylamine, dimethylaniline, diethylaniline, pyridine, picoline, lutidine, collidine, pyrrole, pyrazine, pyrimidine, indolizine, 4-dimethylaminopyridine, or indole in view of the price and/or industrial availability. However, the α-arylethylamine compound (4) itself is preferably used as a base among primary amines to avoid undesired side reactions. Any base selected from these is used alone or in combination thereof. An amount of the base used is from 0.1 to 1000 mol, preferably from 0.5 to 100 mol, more preferably from 0.9 to 10 mol.

The N-2-methylbutylation reaction may be carried out without a solvent, in which either the α-arylethylamine compound (4) or the 2-methylbutylating agent (7) is used in excess to work as a solvent. This solvent-free reaction is preferred because of unnecessity of extra operations such as concentration and/or solvent recovery. The N-2-methylbutylation reaction may be carried out also in a solvent. Examples of the solvent include water; chlorinated solvents such as methylene chloride, chloroform, and trichloroethylene; hydrocarbons such as hexane, heptane, benzene, toluene, xylene, and cumene; ethers such as diethyl ether, dibutyl ether, diethyleneglycol diethyl ether, diethyleneglycol dimethyl ether, tetrahydrofuran, and 1,4-dioxane; alcohols such as methanol, ethanol, 1-propanol, 2-propanol, 1-butanol, 2-butanol, and 2-methyl-2-propanol; nitriles such as acetonitrile; ketones such as acetone and 2-butanone; esters such as ethyl acetate and n-butyl acetate; and aprotic polar solvents such as N,N-dimethylformamide, dimethyl sulfoxide, and hexamethylphosphoric triamide. Any solvent selected from these is used alone or in combination thereof. The N-2-methylbutylation reaction can be also preferably carried out in a biphasic system of water and an organic solvent. An amount of the solvent used is from 0.1 to 5,000 g, preferably from 1 to 500 g, more preferably from 1 to 100 g, per gram of the α-arylethylamine compound (4).

A salt may be used in the N-2-methylbutylation reaction as a catalyst. Example of the salt include metal iodides such as lithium iodide, sodium iodide, potassium iodide, and magnesium iodide; quaternary ammonium salts such as tetramethylammonium hydroxide, tetraethylammonium hydroxide, tetrapropylammonium hydroxide, tetra-n-butylammonium hydroxide, benzyltrimethylammonium hydroxide, tetra-n-butylammonium fluoride, tetra-n-butylammonium chloride, tetra-n-butylammonium bromide, tetra-n-butylammonium iodide, tetra-n-butylammonium hydrosulfate, benzyltriethylammonium chloride, benzyltrimethylammonium bromide, hexadecyltrimethylammonium bromide, benzethonium chloride, benzalkonium chloride, and cetylpyridinium chloride; and quaternary phosphonium salts such as tetra-n-butylphosphonium tetraphenylborate, tri-n-butylcyanomethylphosphonium chloride, tri-n-butyl-n-octylphosphonium bromide, trans-2-butene-1,4-bis(triphenylphosphoniumchloride), and tetraethylphosphonium hexafluorophosphate. The quaternary ammonium salts and quaternary phosphonium salts are effective when used as a phase-transfer catalyst in a biphasic system of water and an organic solvent.

A reaction temperature in the N-2-methylbutylation reaction may be suitably selected depending on the reaction substrate and/or reaction condition to be used, and is preferably from -50° C. to a boiling point temperature of a solvent, more preferably from 0° C. to a boiling point of a solvent, even more preferably from room temperature (5° C. to 35° C., hereinafter the same shall apply) to 100° C.

A reaction time of the N-2-methylbutylation reaction may be arbitrarily set. In view of the yield, it is desirable to monitor the reaction with gas chromatography (GC) and/or silica gel thin layer chromatography (TLC) to complete the reaction. The reaction time is typically from about 0.5 to 720 hours.

It has been found that $^1$H-NMR of the α-arylethyl-2-methylbutylamine compound (2) produced from the N-2-methylbutylation reaction can determine a ratio of a diastereomer at position 2 of the 2-methylbutyl group to a diastereomer at position α of the α-arylethyl group. In other words, it has been found that in the preparation process using an optically active 2-methylbutylating agent (7) as a starting material, the optical purity of at position 2 of the starting 2-methylbutylating agent (7), the optical purity at position 2 of the intermediate α-arylethyl-2-methylbutylamine compound (2) and, ultimately, the optical purity at position 2' of the target compound (1) can be determined when using an optically pure α-arylethylamine compound (4), without using another chiral auxiliary like an α-methoxy-α-(trifluoromethyl)phenylacetyl (MTPA) amide derivative.

It has been also found that in a case where an optically impure 2-methylbutylating agent (7) is used as a starting material, when the optically pure α-arylethylamine compound (4) is used, a mixture of diastereomers (2R*,αR*)-(2) and (2S*,αR*)-(2) of the α-arylethylamine compound of the following general formulae may be separated from the intermediate α-arylethyl-2-methylbutylamine (2) for the purpose of controlling the stereochemical configuration at position 2' of the final target compound 2-methyl-N-(2'-methylbutyl)butanamide (1).

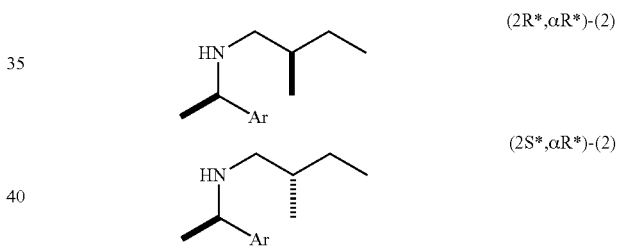

wherein the hashed bond and the bold bonds represent a relative configuration, and Ar is as defined above, to.

The diastereomers are separated and purified by recrystallization and/or various chromatography used in the separation and purification of organic compounds. Examples of the chromatography include gas chromatography (GC), column chromatography, and liquid chromatography (LC). The chromatography is preferably preparative GC and/or preparative LC. The chromatography is particularly preferably preparative high performance liquid chromatography (preparative HPLC). An adsorbent or a stationary phase used in the chromatography may be an achiral carrier or may be a chiral carrier which is used in an optically active stationary phase.

Thus, it has been proved that the α-arylethylamine compound (4) functions not only as a nitrogen source for amine synthesis but also as a chiral auxiliary for the determination of stereoisomeric purity and further functions as a chiral auxiliary for optical resolution.

The α-arylethyl-2-methylbutylamine compound (2) thus prepared may be separated and purified in any purification method used in usual organic synthesis, such as distillation and/or various chromatography. Distillation is preferred for the industrial mass production in view of the economy.

When the compound (2) has a sufficient purity, the compound (2) may be used as such in a subsequent step.

The α-arylethyl-2-methylbutylamine compound (2) is preferably a (2S)-α-arylethyl-2-methylbutylamine compound of the following general formula (2S)-(2), because this stereochemical form contains the natural sex pheromone exhibiting attracting activity.

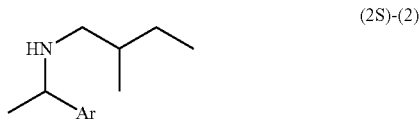

Step of subjecting an α-arylethyl-2-methylbutylamine compound to N-2-methylbutyrylation

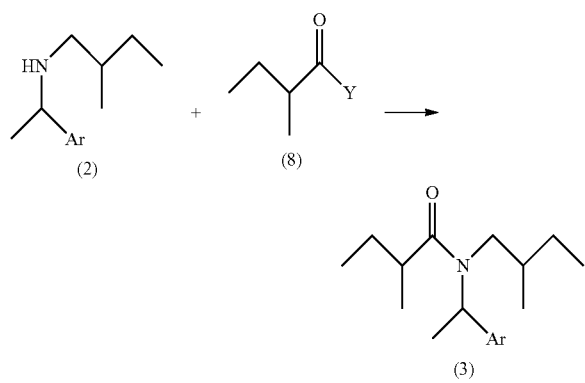

wherein Y represents a leaving group, and Ar is as defined above.

In this step, the α-arylethyl-2-methylbutylamine compound (2) is subjected to N-2-methylbutyrylation with an N-2-methylbutyrylating agent (8) to form an N-α-arylethyl-2-methyl-N-(2'-methylbutyl)butanamide compound (3).

Ar in the α-arylethyl-2-methylbutylamine compound (2) is as defined in the α-arylethylamine compound (4).

The leaving group Y in the N-2-methylbutyrylating agent (8) may be selected from any leaving groups that are known to cause N-acylation (amide synthesis). Examples include, but are not particularly limited to, a halo group, an alkanesulfonyloxy group, an arenesulfonyloxy group, a dialkylphosphoryloxy group, a diarylphosphoryloxy group, an acyloxy group, an alkoxycarbonyloxy group, an imidazolyl group and groups having quaternized salts thereof, and a group causing the N-2-methylbutyrylating agent (8) to be an activated ester, such as a p-nitrophenyloxy group, a 3,5-dinitrophenyloxy group, and a p-chlorophenyloxy group.

Preferred examples of the 2-methylbutyrylating agent (8) include 2-methylbutanoic acid halides such as 2-methylbutyryl chloride, 2-methylbutyryl bromide, and 2-methylbutyryl iodide; 2-methylbutanoic/carboxylic acid mixed anhydrides such as 2-methylbutyric anhydride (2-methylbutanoic acid anhydride), acetic 2-methylbutyric anhydride, formic 2-methylbutyric anhydride, 2-methylbutyric trichloroacetic anhydride, and 2-methylbutyric trifluoroacetic anhydride; 2-methylbutanoic/carbonic acid mixed anhydrides such as ethylcarbonic 2-methylbutyric anhydride and 2-methylbutyric methylcarbonic anhydride; 2-methylbutanoic/sulfonic acid mixed anhydrides such as methanesulfonic 2-methylbutyric anhydride, butanesulfonic 2-methylbutyric anhydride, 2-methylbutyric trifluoromethanesulfonic anhydride, benzenesulfonic 2-methylbutyric anhydride, and 2-methylbutyric p-toluenesulfonic anhydride; 2-methylbutanoic/sulfuric acid mixed anhydrides such as ethylsulfuric 2-methylbutyric anhydride and 2-methylbutyric methylsulfuric anhydride; 2-methylbutanoic/phosphoric acid mixed anhydrides such as diethylphosphoric 2-methylbutyric anhydride, dimethylphosphoric 2-methylbutyric anhydride, and 2-methylbutyric diphenylphosphoric anhydride; and 2-methylbutyrylimidazole and quaternized salts thereof. The 2-methylbutyrylating agent (8) can be selected from these in view of the reactivity, the price, the industrial availability, the storage stability, and the odor. 2-Methylbutanoic acid halides, 2-methylbutyric anhydride, 2-methylbutanoic/carboxylic acid mixed anhydrides, 2-methylbutanoic/carbonic acid mixed anhydrides, 2-methylbutanoic/phosphoric acid mixed anhydrides, and 2-methylbutanoic/sulfonic acid mixed anhydrides are particularly preferred. However, when the N-2-methylbutyrylating agent (8) is an optically active substance, 2-methylbutanoic acid halides should be avoided because of the risk of racemization. The 2-methylbutyrylating agent (8) may be its (±)-form or its optically active (R)- or (S)-form having any optical purity. The N-2-methylbutyrylating agent (8) may be commercially available one or may be prepared in house. In the latter case, the N-2-methylbutyrylating agent (8) may be prepared in advance or in situ.

The N-2-methylbutyrylation reaction is typically allowed to proceed by adding sequentially or simultaneously the α-arylethyl-2-methylbutylamine compound (2) and the 2-methylbutyrylating agent (8) in the presence of a base in a solvent or without a solvent, with heating or cooling.

An amount of the α-arylethyl-2-methylbutylamine compound (2) used may be optionally set and is typically from 0.02 to 500 mol, preferably from 0.2 to 50 mol, more preferably from 0.9 to 5 mol, per mol of the 2-methylbutyrylating agent (8). When the unreacted remaining α-arylethyl-2-methylbutylamine compound (2) can be recovered, the α-arylethyl-2-methylbutylamine compound (2) is preferably used in excess relative to the 2-methylbutyrylating agent (8) to completely consume the 2-methylbutyrylating agent (8), in view of the yield and/or efficiency.

The base used in the N-2-methylbutyrylation reaction is an inorganic base or an organic base. Examples of the base include bases exemplified in the description of the step of subjecting an α-arylethylamine compound to N-2-methylbutylation. An α-arylethyl-2-methylbutylamine compound (2) that is a secondary amine is preferably used as a base to avoid undesired side reactions. Any base selected from these is used alone or in combination thereof An amount of the base used is from 0.1 to 1000 mol, preferably from 0.5 to 100 mol, more preferably 0.9 to 10 mol.

The N-2-methylbutyrylation reaction may be carried out without a solvent, in which either the α-arylethyl-2-methylbutylamine compound (2) or the 2-methylbutyrylating agent (8) is used in excess to work as a solvent. This solvent-free reaction is preferred because of unnecessity of extra operations such as concentration and/or solvent recovery. The N-2-methylbutyrylation reaction may be also carried out in a solvent. The solvent may be selected from those exemplified in the description of the step of subjecting an α-arylethylamine compound to N-2-methylbutylation. An amount of the solvent used is from 0.1 to 5,000 g, preferably from 1 to 500 g, more preferably 1 to 100 g, per gram of the α-arylethyl-2-methylbutylamine compound (2).

A salt may be used in the N-2-methylbutyrylation reaction as a catalyst. Examples of the salt include those exemplified in the description of the step of subjecting an α-arylethyl-amine compound to N-2-methylbutylation. In particular, the quaternary ammonium salts and quaternary phosphonium salts are effective when used as a phase-transfer catalyst in a biphasic system of water and an organic solvent.

A reaction temperature in the N-2-methylbutyrylation reaction may be suitably selected depending on the reaction substrate and/or reaction condition to be used, and is preferably from -50° C. to a boiling point temperature of a solvent, more preferably from 0° C. to a boiling point of a solvent, even more preferably from room temperature (5° C. to 35° C., hereinafter the same shall apply) to 100° C.

A reaction time of the N-2-methylbutyrylation reaction may be arbitrarily set. In view of the yield, it is desirable to monitor the reaction with gas chromatography (GC) and/or silica gel thin layer chromatography (TLC) to complete the reaction. The reaction time is typically from about 0.5 to 720 hours.

The N-α-arylethyl-2-methyl-N-(2'-methylbutyl)butanamide compound (3) thus prepared may be isolated or purified in any purification method used in usual organic synthesis, such as distillation and/or various chromatography. Distillation is preferred for the industrial mass production in view of the economy. When the compound (3) has a sufficient purity, the compound (3) may be used as such in a subsequent step.

The N-α-arylethyl-2-methyl-N-(2'-methylbutyl)butanamide compound (3) thus prepared is preferably a (2S)-N-α-arylethyl-2-methyl-N-(2'-methylbutyl)butanamide compound of the following general formula (2S)-(3), a (2'S)-N-α-arylethyl-2-methyl-N-(2'-methylbutyl)butanamide compound of the following general formula (2'S)-(3), or a (2S,2'S)-N-α-arylethyl-2-methyl-N-(2'-methylbutyl)butanamide compound of the following general formula (2S,2'S)-(3), because these stereochemical forms are contained in the natural sex pheromone exhibiting attracting activity.

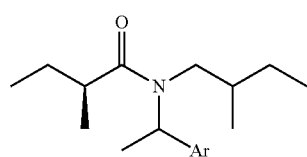

(2S)-(3)

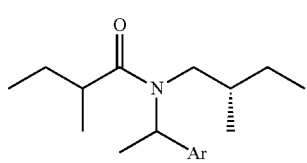

(2'S)-(3)

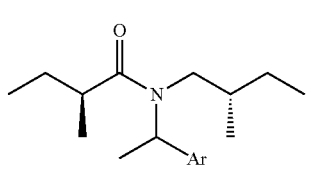

(2S,2'S)-(3)

Step of removing the α-arylethyl group of the N-α-arylethyl-2-methyl-N-(2'-methylbutyl)butanamide compound

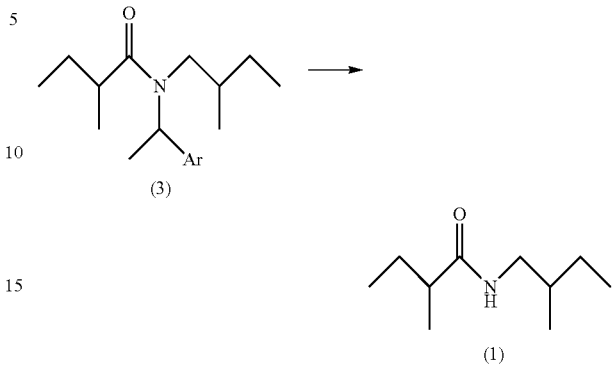

wherein Ar is as defined above.

In this step, the α-arylethyl group of the N-α-arylethyl-2-methyl-N-(2'-methylbutyl)butanamide compound (3) thus prepared is subjected to a removal reaction to form the target compound, 2-methyl-N-(2'-methylbutyl)butanamide (1).

Ar in the N-α-arylethyl-2-methyl-N-(2'-methylbutyl)butanamide compound (3) is as defined for the α-arylethyl-amine compound (4).

In the removal reaction of the α-arylethyl group, the N-α-arylethyl-2-methyl-N-(2'-methylbutyl)butanamide compound (3) is typically heated or cooled in the presence of an acid in a solvent or without a solvent to form 2-methyl-N-(2'-methylbutyl)butanamide (1).

The acid used in the removal reaction of the α-arylethyl group is preferably a Bronsted acid. Examples of the acid include inorganic acids such as hydrochloric acid, hydrobromic acid, perchloric acid, sulfuric acid, nitric acid, and phosphoric acid; carboxylic acids such as formic acid, acetic acid, propionic acid, butyric acid, hexanoic acid, oxalic acid, and trifluoroacetic acid; and sulfonic acids such as methanesulfonic acid, benzenesulfonic acid, and p-toluenesulfonic acid. Among these acids, carboxylic acids are preferred. In the acid removal reactions with carboxylic acids, the α-arylethyl group is converted into an α-arylethyl ester (α-arylethyl carboxylate). Formic acid is particularly preferred in view of the ease of removal of α-arylethyl formate to be produced by separation and/or purification such as distillation.

An amount of the acid used may be less than a stoichiometric amount, but in this case, an α-arylethyl group will be converted mainly into a corresponding vinylarene. A polymer of the vinylarene may prevent purification of the target compound. On the other hand, when the acid is used in an amount greater than a stoichiometric amount, a corresponding α-arylethyl ester is formed as described above, which is preferable because the corresponding α-arylethyl ester can be easily removed from the target compound in any conventional method such as distillation and/or chromatography. An amount of the acid used is from 0.01 to 10000 mol, preferably from 0.1 to 1000 mol, more preferably 1 to 100 mol.

The removal reaction of the α-arylethyl group may be carried out without a solvent. The carboxylic acid used in the reaction may be used to work as a solvent. An auxiliary solvent may be further used to transfer substances, to remove the heat, or to adjust the concentration. Examples of the auxiliary solvent include chlorinated solvents such as methylene chloride, chloroform, and trichloroethylene; hydrocarbons such as hexane, heptane, benzene, toluene, xylene, and cumene; ethers such as diethyl ether, dibutyl ether, diethyleneglycol diethyl ether, diethyleneglycol dimethyl ether, tetrahydrofuran, and 1,4-dioxane; nitriles such as acetonitrile; ketones such as acetone and 2-butanone; esters such as ethyl acetate and n-butyl acetate; and aprotic polar solvents such as N,N-dimethylformamide, dimethyl sulfoxide, and hexamethylphosphoric triamide. Any solvent selected from these is used alone or in combination thereof. An amount of the solvent used is from 0.1 to 5,000 g, preferably from 1 to 500 g, more preferably from 1 to 100 g, per gram of the α-arylethylamine compound (4).

A reaction temperature in the removal reaction of the α-arylethyl group may be suitably selected depending on the acid to be used and/or the α-arylethyl ester to be produced and/or the reaction condition, and is preferably from -50° C. to a boiling point temperature of a solvent, more preferably from −20° C. to room temperature (5° C. to 35° C., hereinafter the same shall apply). In the removal reaction carried out by heating and distilling off the resulting α-arylethyl ester in normal pressure or a reduced pressure at a temperature higher than its boiling point, further continuing distillation allows isolation of the target compound. Therefore, such removal reaction is industrially very useful.

A reaction time of the removal reaction of an α-arylethyl group may be arbitrarily set. In view of the yield, it is desirable to monitor the reaction with gas chromatography (GC) and/or silica gel thin layer chromatography (TLC) to complete the reaction. The reaction time is typically from about 0.5 to 720 hours.

2-Methyl-N-(2'-methylbutyl)butanamide (1) thus prepared may be isolated or purified in any purification method used in usual organic synthesis, such as distillation and/or various chromatography. Distillation is preferred for the industrial mass production in view of the economy.

2-Methyl-N-(2'-methylbutyl)butanamide (1) thus prepared is preferably (2S)-2-methyl-N-(2'-methylbutyl)butanamide of the following formula (2S)-(1), (2'S)-2-methyl-N-(2'-methylbutyl)butanamide of the following formula (2'S)-(1), or (2S,2'S)-2-methyl-N-(2'-methylbutyl)butanamide of the following formula (2S,2'S)-(1), because these stereochemical forms are contained in the natural sex pheromone exhibiting activity of attracting *Migdolus fryanus*.

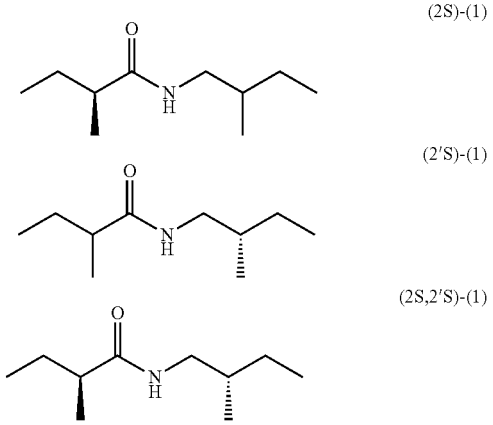

Comparison with a preparation process using a benzyl group as a protecting group.

The present inventors also investigated use of a benzyl group as a protecting group R in the plan for synthesis in the early stage of investigation of a process for preparing the target compound of the present invention, 2-methyl-N-(2'-methylbutyl)butanamide (1). The process using a benzyl group as a protecting group R will be described below for comparison with the preparation process of the present invention using an α-arylethyl group as a protecting group R.

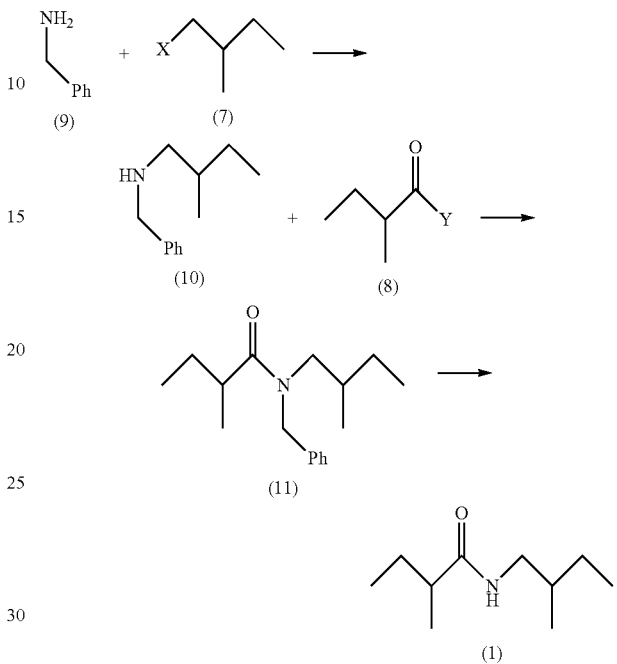

wherein Ph represents a phenyl group (hereinafter the same).

The intermediates, benzyl-2-methylbutylamine (10) and N-benzyl-2-methyl-N-(2'-methylbutyl)butanamide (11) may be prepared using benzylamine (9) as a starting material in steps similar to those as mentioned in the preparation of the α-arylethyl-2-methylbutylamine compound (2) and the N-α-arylethyl-2-methyl-N-(2'-methylbutyl)butanamide compound (3), respectively.

The present inventors investigated the conversion of N-benzyl-2-methyl-N-(2'-methylbutyl)butanamide (11) thus prepared into the target compound 2-methyl-N-(2'-methylbutyl)butanamide (1) via a removal reaction of the benzyl group (debenzylation) of the benzylamine compound. Catalytic hydrogenolysis, which is thought to be most common for the debenzylations, was investigated in various conditions such as metal catalyst species, solvents, temperatures, and additives, but all of the conditions resulted in slow reaction rates of and the reaction stopped in a low of conversion. This is possibly because the produced amine itself makes the reaction catalyst poisoned. Various known debenzylation reactions such as oxidative debenzylation were also investigated, and some of the reactions gave the target compound, but in an insufficient yield. The reaction examples will be described below in Comparative Examples of the preparation processes.

Advantages of the process of the present invention for preparing 2-methyl-N-(2'-methylbutyl)butanamide as described above include, for example:

(1) comprising fewer steps and achieving a high yield and a high efficiency;

(2) unnecessity of 2-methylbutylamine, which is difficult to handle due to its high volatility, has a bad smell, and is expensive, both as a starting material and as a synthesis intermediate;

(3) the starting material, α-arylethyl-2-methylbutylamine compound, is easily prepared, for example, from 2-methylbutanol or 1-halo-2-methylbutane and those compounds are industrially available in inexpensive (±)-form as well as in an optically active form;

(4) the starting material, α-arylethylamine compound, is industrially available at a low price in a (±)-form, (R)-form, and (S)-form;

(5) being applicable to both the preparation of a mixture of diastereomers and the preparation of an optically active substance by controlling the configuration of stereogenic center(s) at either position 2 or 2' or both;

(6) the optical purity of diastereomers at position 2' may be determined when an optically pure α-arylethylamine is used in the preparation process that is carried out by controlling the configuration of the stereogenic center at position 2';

(7) able to the enhance optical resolution and/or optical purity of diastereomers at position 2' by appropriately selecting optically active α-arylethylamine;

(8) suppressing a decrease of the optical purity of diastereomers at position 2 at which epimerization may occur in the removal of an α-arylethyl group in the preparation process that is carried out while controlling the configuration of the stereogenic center at position 2; and (9) the removal of an α-arylethyl group used as a protecting group proceeds in relatively moderate reaction conditions compared to removal of a benzyl group widely used in various amine syntheses.

It should be noted that advantages (4), (6), and (7) as well as advantage (9) are in principle impossible in the preparation process using a benzyl group. Therefore, the preparation process of the present invention using an α-arylethyl group is superior to the preparation process using a benzyl group.

Thus, the process for efficiently and industrially practically preparing 2-methyl-N-(2'-methylbutyl)butanamide have been successfully established.

EXAMPLES

The present invention will be further described with reference to the following Examples. It should be noted that the present invention is not limited to or by the Examples.

Purities of raw materials, products, and intermediates were determined by gas chromatography (GC) and are expressed in % GC. An isomer ratio of products or intermediates is a ratio of peak areas determined by GC. GC conditions: GC: Shimadzu GC-2025, Column: 5% Ph-Me silicone 25 m×0.25 mmφ×0.25 μm, Carrier gas: He, Detector: FID Yield is a reduced yield calculated based on % GC. Because raw materials used in reactions and products obtained in reactions do not always have a purity of 100%, a yield is calculated by the following equation: Reduced Yield (%)={[(mass of a product obtained in a reaction ×% GC)/molecular mass of a product]÷[(mass of a raw material used in a reaction ×% GC)/molecular mass of a raw material]}×100. Detection sensitivities in gas chromatography may differ among compounds, so that reduced yields may sometimes exceed 100%, particularly when raw materials or products are crude.

Crude materials were purified to obtain samples for observing spectra of the materials, where necessary.

Preparation of (2S,2'S)-2-methyl-N-(2'-methylbutyl)butanamide: (2S,2'S)-(1)

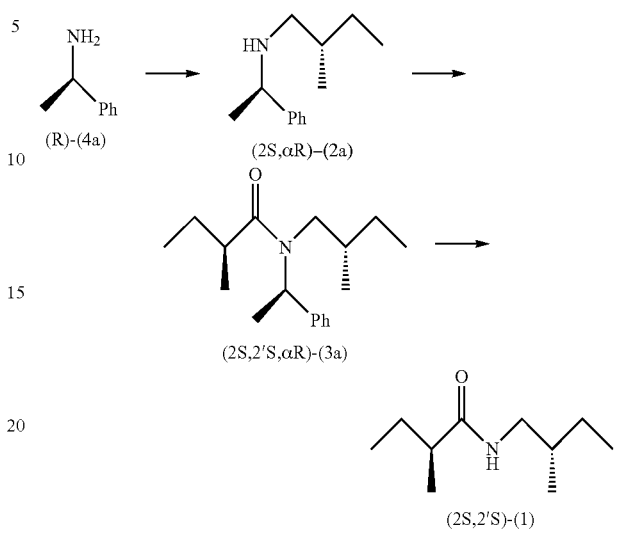

wherein Ph represents a phenyl group (hereinafter the same).

Example 1: Preparation of (2S,αR)-2-methylbutyl-α-phenylethylamine: (2S,αR)-(2a) (Ar=Ph=phenyl group in the general formula (2))

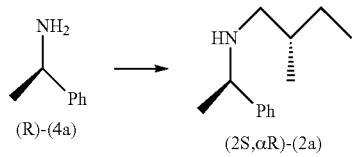

A mixture of 52.8 g of (S)-2-methylbutyl p-toluenesulfonate prepared in a conventional method from (S)-2-methylbutanol (99.1% S, 98.2% ee) and 70.6 g of (R)-α-phenylethylamine (~100% ee) was stirred at 90 to 100° C. for 17 hours in a nitrogen atmosphere. The reaction mixture was cooled, diluted with 100 ml of tert-butyl methyl ether, and poured into an aqueous 5% sodium hydroxide solution. The organic layer was separated, and the aqueous layer was subjected to extraction with tert-butyl methyl ether. The combined organic layers were concentrated, and the concentrate was distilled at a reduced pressure to recover 39 g of (R)-α-phenylethylamine and obtain 37.6 g of the target compound (2S,αR)-(2a) (99.3% GC, yield 90%; total yield of fractions 92%).

(2S,αR)-2-Methylbutyl-α-phenylethylamine: (2S,αR)-(2a): $C_{13}H_{21}N$

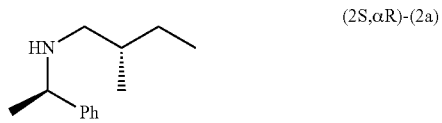

Colorless oil.
Boiling point: 67° C./0.3 kPa.
Specific rotation: $[\alpha]_D^{22}$+67.5(c=1.0,CHCl$_3$)

IR (D-ATR): ν=3083, 3063, 2960, 2925, 2874, 2810, 1603, 1463, 1452, 1369, 1305, 1210, 1128, 1028, 910, 760, 700, 597, 555 cm$^{-1}$.

$^1$H-NMR (600 MHz, CDCl$_3$):δ=0.85 (3H, t, J=7.4 Hz), 0.88 (3H, d,J=6.7 Hz), 1.07-1.15 (1H, m), 1.2-1.8 (1H, NH, broad), 1.321.41 (1H, m), 1.35 (3H, d, J=6.6 Hz), 1.45-1.54 (1H, m), 2.18 (1H, dd, J=11.5, 7.7 Hz), 2.45 (1H, dd, J=11.5, 5.5 Hz), 3.73 (1H, q, J=6.6 Hz), 7.21-7.25 (1H, m), 7.30-7.35 (4H, m) ppm.

Of the $^1$H-NMR spectral signals, the signals derived from two diastereotopic hydrogen atoms at position 1 of a major diastereomer (2S,αR)-(2a) were observed at δ=2.18 (1H, dd, J=11.5, 7.7 Hz) and 2.45 (1H, dd, J=11.5, 5.5 Hz). The signals derived from two diastereotopic hydrogen atoms at position 1 of a minor diastereomer (2R,αR)-(2a) (this minor diastereomer is derived from (R)-2-methylbutanol, which is an opposite enantiomer of the starting material (S)-2-methylbutanol and is present in a minor amount in the starting material) were observed at δ=2.31 (1H, dd, J=11.5, ~6.6 Hz) and 2.33 (1H, dd, J=11.5, ~6.6 Hz). The ratio of the diastereomers resulting from the stereochemical configuration at position 2 was estimated by calculation from the integrated areas under these peaks to be major:minor=(2S, αR):(2R,αR)=98.54: 1.46. The strong $^{13}$C satellite peaks overlapped with this chemical shift range were exclude from this calculation.

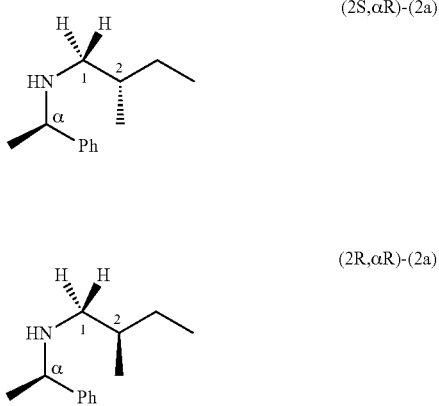

(2S,αR)-(2a)

(2R,αR)-(2a)

This isomer ratio indicated that the stereochemical configuration of the stereogenic center at position 2 of the starting material was maintained without isomerization.

It was also showed that when optically pure α-phenylethylamine was used as a starting material, the absolute configuration of the stereogenic center at position 2 and the optical purity can be determined from this compound itself without conversion into another derivative.

$^{13}$C-NMR (150 MHz, CDCl$_3$): δ=11.53, 17.87, 24.70, 27.76, 35.15, 54.06, 58.58, 126.71(2C), 126.88, 128.49 (2C), 146.17 ppm.

GC-MS (EI, 70 eV): 30, 41, 51, 65, 77, 91, 105 (base peak), 118, 134, 176, 191 (M$^+$).

Example 2: Preparation of (2S,2'S,αR)-2-methyl-N-(2-methylbutyl)-N-(α-phenylethyl)butanamide: (2S,2'S,αR)-(3a) (Ar=Ph in the general formula (3))

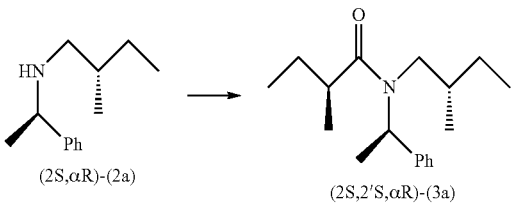

(2S,αR)-(2a)

(2S,2'S,αR)-(3a)

A mixture of 10.25 g of (S)-2-butanoic acid (99.3% S, 98.5% ee), 30.5 g of triethylamine, and 80 ml of tetrahydrofuran was cooled with ice in a nitrogen atmosphere, and 26.9 g of diphenylphosphoryl chloride was added dropwise to the mixture at 15° C. or lower for 5 minutes. The mixture was stirred at 7° C. for 10 minutes and then at room temperature for 20 minutes. The resulting crystals were filtered off through celite, and the cake was washed with 30 ml of tetrahydrofuran. To the combined filtrates were added 18.0 g of (2S,αR)-(2a) obtained in Example 1 and 61 g of triethylamine at room temperature in a nitrogen atmosphere with stirring. The mixture was stirred at 72 to 75° C. for 24 hours. The reaction mixture was concentrated at a reduced pressure to remove tetrahydrofuran and triethylamine. The residue was dissolved in diethyl ether, and the ether solution was washed with dilute hydrochloric acid, water, a saturated aqueous solution of sodium bicarbonate, and saturated brine, dried over magnesium sulfate, and concentrated at a reduced pressure. The concentrate was purified by silica gel column chromatography to obtain 23.98 g of the target compound (2S,2'S,αR)-(3a) (93.8 to 98.8% GC, yield 91%).

(2S,2'S,'R)-2-Methyl-N-(2-methylbutyl)-N-(α-phenylethyl)butanamide: (2S,2'S,αR)-(3a): C$_{18}$H$_{29}$NO

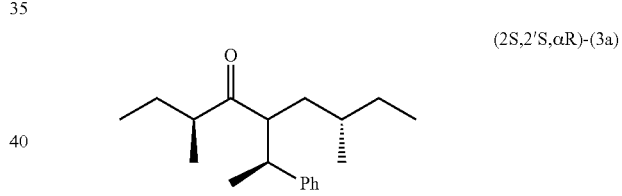

(2S,2'S,αR)-(3a)

Colorless oil.

Specific rotation: [α]D$^{22}$+105.0 (c=1.0, CHCl$_3$).

IR (D-ATR): ν=3063, 3030, 2963, 2933, 2874, 1737, 1639, 1496, 1463, 1417, 1379, 1301, 1271, 1231, 1207, 1185, 1157, 1117, 1088, 1049, 1028, 970, 911, 787, 745, 699 cm$^{-1}$.

$^1$H-NMR (600 MHz, CDCl$_3$): δ=0.74 (3×0.55H, d, J=6.7 Hz), 0.771 (3×0.45H, t, J=7.3 Hz), 0.772 (3×0.45H, d, J=6.7 Hz), 0.78 (3×0.55H, t, J=7.3 Hz), 0.84-0.90 (0.55H, m), 0.89 (3H, t, J=7.4 Hz), 0.90-0.99 (0.45H, m), 1.07 (3×0.45H, d, J=6.8 Hz), 1.11 (3×0.55H, d, J=6.7 Hz), 1.12-1.29 (2×0.55H+0.45H, m), 1.39-1.47 (0.45H+0.55H, m), 1.52-1.58 (0.45H, m)1.56 (3×0.55H, d, J=7.2 Hz), 1.65 (3×0.45H, d, J=7.1 Hz), 1.66-1.75 (0.55H, m), 1.75-1.84 (0.45H, m), 2.63 (0.55H, hex-like, J=~6.8 Hz), 2.67 (0.45H, hex-like, J=6.8 Hz), 2.88 (0.45H, dd, J=13.6, 8.4, Hz), 2.91 (0.55H, dd, J=15.1, 8.5 Hz), 3.04 (0.55H, dd, J=15.1, 7.0 Hz), 3.23 (0.45H, dd, J=13.6, 6.6 Hz), 5.16 (0.45H, q, J=7.0 Hz), 5.83 (0.55H, q, J=7.1 Hz), 7.21-7.36 (5H, m) ppm.

In the $^1$H-NMR, diastereomers, which were tautomers, of the obtained compound were present in the sample in CDCl$_3$ at a ratio of ~55:45, and each of the diastereomers gave different peaks. This phenomenon occurred because the sample contained the diastereomers resulting from the nitrogen stereogenic center as shown in the following formulae. This amine compound has such diastereomers because it has three different substituents and a lone pair on the nitrogen atom undergoing sp3 hybridization, so that rapid inversion of the nitrogen stereogenic center is inhibited due to the steric hindrance of the bulky substituents. The number of hydrogen atoms in the $^1$H-NMR data is described so that the number representing a single hydrogen atom of these diastereomers is converted into 0.55H or 0.45H based on a coefficient and the total number of hydrogen atoms is 29H. The coefficient is equivalent to the integrated value.

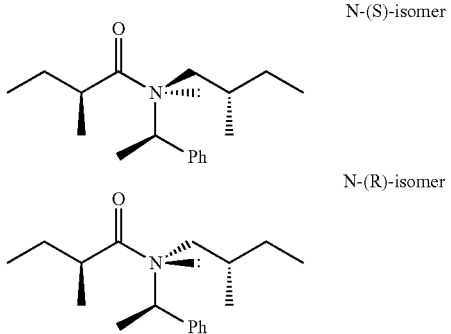

wherein ":" represents a lone pair.

$^{13}$C-NMR (150 MHz, CDCl$_3$): δ=11.62, 11.73, 12.12, 12.38, 17.07, 17.16, 17.44, 17.63, 18.25, 19.39, 27.08, 27.48, 27.55, 27.67, 34.05, 35.18, 37.82, 38.53, 49.80, 50.54, 52.56, 55.31, 126.93 (2C), 127.27, 127.54, 127.84 (2C), 128.34 (2C), 128.69 (2C), 141.55, 141.65, 177.76, 178.11 ppm.

Each of the diastereomers resulting from the asymmetric nitrogen atom gave different signals in the $^{13}$C-NMR. The signals assigned to the major diastereomer are underlined.

GC-MS (EI, 70 eV): 41, 57, 79, 105 (base peak), 120, 134, 156, 177, 204, 218, 275 (M$^+$).

Example 3: Preparation of (2S,2'S)-2-methyl-N-(2-methylbutyl)butanamide: (2S,2'S)-(1)

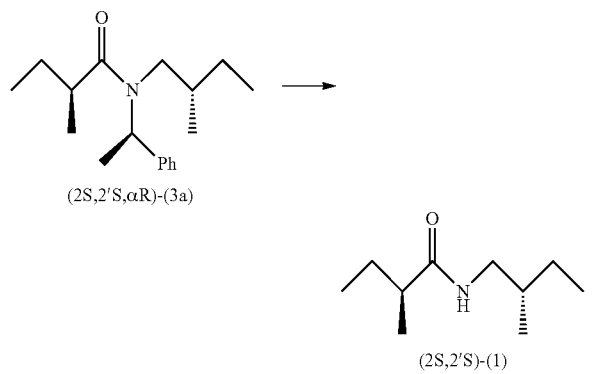

A mixture of 3.90 g of (2S,2'S,αR)-(3a) obtained in Example 2 and 14.0 g of formic acid was heated to 70 to 75° C. for 12 hours in a nitrogen atmosphere with stirring. The reaction mixture was cooled to 50° C. and then distilled at a reduced pressure in a reaction vessel equipped with a distillation head to obtain unreacted remaining formic acid and α-phenylethyl formate as fractions, followed by 1.89 g of the target compound (2S,2'S)-(1) (92.0% GC, yield 79%).

(2S,2'S)-2-Methyl-N-(2-methylbutyl)butanamide: (2S,2S)-(1): C$_{10}$H$_{21}$NO

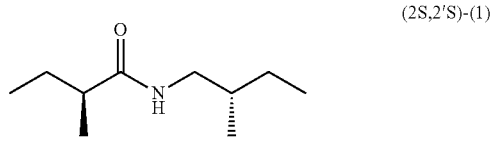

Colorless oil.

Specific rotation: [α]D$^{25}$+23.3 (c=3.0, CH$_3$CH$_2$OCH$_2$CH$_3$)

IR (D-ATR): ν=3297, 3087, 2963, 2932, 2876, 1732, 1645, 1553, 1462, 1381, 1269, 1236, 1108, 968, 765, 699 cm$^{-1}$.

$^1$H-NMR (600 MHz, CDCl$_3$): δ=0.89 (3H, d, J=6.7 Hz), 0.897 (3H, t, J=7.5 Hz), 0.899 (3H, t, J=7.5 Hz), 1.13 (3H, d, J=6.9 Hz), 1.12-1.19 (1H, m), 1.35-1.46 (2H, m), 1.49-1.59 (1H, m), 1.62-1.70 (1H, m), 2.02-2.14 (1H, m), 3.09 (1H, dt-like, J=~13.4, ~6.5 Hz), 3.17 (1H, dt-like, J=~13.4, ~6.0 Hz), 5.46 (1H, NH, br.s) ppm.

Of the $^1$H-NMR spectral signals, the signals derived from hydrogen atoms at position 1 of the major diastereomer (2S,2'S)-(1) (and more precisely a trace amount of (2R,2'R)-(1)) were observed at δ=3.09 (1H, dt-like, J=~13.4, ~6.5 Hz) and 3.17 (1H, dt-like, J=~13.4, ~6.0 Hz). The corresponding signals of minor diastereomers (2R,2'S)-(1) and (2S,2'R)-(1) were observed at δ=3.04 (1H, dt-like, J=~13.4, ~7 Hz) and 3.23 (1H, dt-like, J=~13.4, ~7 Hz). The ratio of the diastereomers resulting from the stereochemical configuration at position 2 was estimated to be [(2S,2'S)+(2R,2'R)]: [(2R,2'S)+(2S,2'R)]=91:9 by calculation from the integrated areas under these peaks. $^{13}$C-NMR (150 MHz, CDCl$_3$): δ=11.42, 12.11, 17.31, 17.80, 27.15, 27.52, 35.10, 43.63, 45.00, 176.56 ppm. GC-MS (EI, 70 eV): 41, 57 (base peak), 71, 85, 102, 114, 128, 143, 156, 171 (M$^+$).

Chiral phase GC: HP 7890B, Column: Cyclosil-B 30 m×0.25 mmϕ×0.25 μm, 130° C. const., carrier gas: He 1 mL/min, Inj: 220° C., detector: FID 230° C.: 6.56% (Rt 17.57 min), 93.43% (Rt 18.11 min). In this GC, the stereochemical configurations at position 2 in the acyl moiety gave separate peaks. Thus, the ratio of the stereochemical configurations at position 2 was estimated to be [(2R,2'R)+(2R,2'S)] : [(2S,2'S) +(2S,2'R)]=93.43 : 6.56.

The configuration ratio at position 2' was calculated from the diastereomer ratio determined in the $^1$H-NMR and the configuration ratio at position 2 determined in the chiral phase GC. The configuration at position 2 was determined to be 93.44% S, and the configuration at position 2' was determined to be 97.19% S (i.e., 90.99% de, 99.80% ee) as shown below. The results demonstrate that the preparation process of the present invention enables the preparation of the target compound in a high optical purity without racemization nor epimerization.

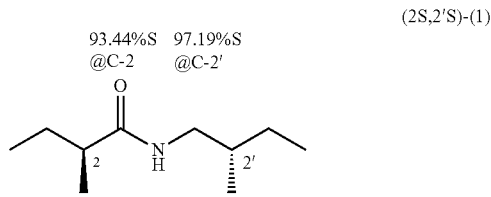

Preparation of (2S,2'RS)-2-methyl-N-(2'-methylbutyl)butanamide: (2S,2'RS)-(1)

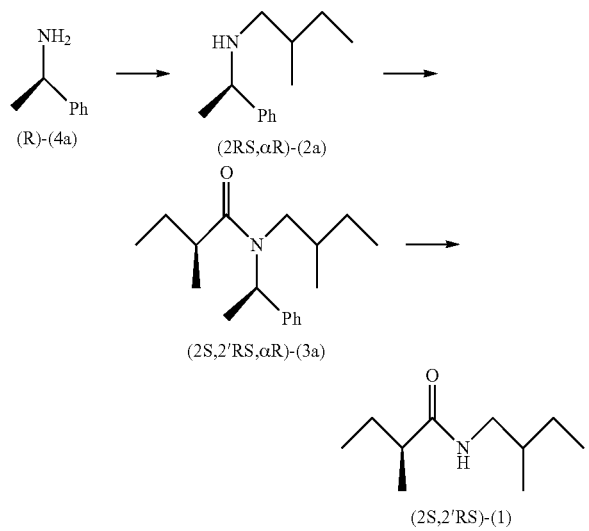

Example 4: Preparation of (2RS,αR)-2-methylbutyl-α-phenylethylamine: (2RS,αR)-(2a) (a 50:50 mixture of (2R,αR)-(2a) and (2S,αR)-(2a), Ar=Ph in the general formula (2))

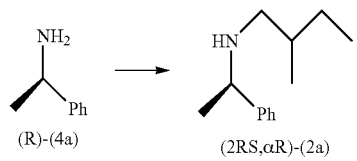

The procedures of Example 1 were repeated with the exception that 135 g of (±)-2-methylbutyl p-toluenesulfonate was used instead of (S)-2-methylbutyl p-toluenesulfonate used in Example 1, so that obtained was 96.3 g of the target compound (2RS,αR)-(2a) (99.7% GC, yield 90%; total yield of fractions 93%). (2RS,αR)-2-Methylbutyl-α-phenylethylamine: (2RS,αR)-(2a) (a 50:50 mixture of (2R,αR)-(2a) and (2S,αR)-(2a)): $C_{13}H_{21}N$

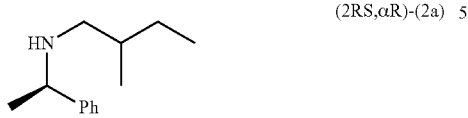

Colorless oil.
Boiling point: 69° C./0.3 kPa.
Specific rotation: $[\alpha]D^{26}$+59.3 (c=1.0, CHCl$_3$).
IR (D-ATR): ν=3083, 3062, 3025, 2960, 2925, 2874, 2810, 1603, 1493, 1452, 1369, 1305, 1210, 1127, 1028, 910, 760, 700, 597, 555 cm$^{-1}$.
$^1$H-NMR (600 MHz, CDCl$_3$): δ=0.846 (3×0.5H, t, J=7.4 Hz), 0.850 (3×0.5H, t, J=7.4 Hz), 0.87 (3×0.5H, d, J=~6 Hz), 0.88 (3×0.5H, d, J=~6 Hz), 1.06-1.16 (1H, m), 1.2-1.6 (1H, NH, br.), 1.32-1.46 (1H, m), 1.35 (3H, d, J=6.6 Hz), 1.46-1.54 (1H, m), 2.18 (0.5H, dd, J=11.5, 7.7 Hz), 2.31 (0.5H, dd, J=11.5, 6.6 Hz), 2.33 (0.5H, dd, J=11.5, 6.6 Hz), 2.45 (0.5H, dd, J=11.5, 5.5 Hz), 3.73 (1H, q, J=6.6 Hz), 7.21-7.25 (1H, m), 7.30-7.35 (4H, m) ppm. The number of hydrogen atoms in the $^1$H-NMR data is described so that the number representing a single hydrogen atom of the two diastereomers is converted into 0.5H based on a coefficient and the total number of hydrogen atoms is 21H. The coefficient is equivalent to the integrated value. Hereinafter, data for a mixture of diastereomers are described in a similar manner.
$^{13}$C-NMR (150 MHz, CDCl$_3$): δ=11.32 (0.5C), 11.52, (0.5C), 17.81 (0.5C), 17.86 (0.5C), 24.64 (0.5C), 24.72 (0.5C), 27.40 (0.5C), 27.75 (0.5C), 35.11 (0.5C), 35.16 (0.5C), 54.06 (0.5C), 54.12 (0.5C), 58.57 (0.5C), 58.62 (0.5C), 126.70 (2C), 126.86 (1C), 128.47 (2C), 146.22 (1C) ppm. The number of hydrogen atoms in the $^{13}$C-NMR data is described so that the number representing a single carbon atom of the two diastereomers is converted into 0.5C based on a coefficient and the total number of carbon atoms is 13C. The coefficient does not necessarily correlate with a peak intensity and an integrated value. Hereinafter, $^{13}$C-NMR data for a mixture of diastereomers are described in a similar manner.
GC-MS (EI, 70 eV): 30, 41, 51, 65, 77, 91, 105 (base peak), 118, 134, 176, 191 (M$^+$).
The specific rotation of (R)-α-phenylethylamine: (R)-(4a) used in the reaction and the unreacted remaining thereof recovered after the reaction were as follows:
Used (R)-(4a): $[\alpha]D^{26}$+38.7 (neat)
Recovered (R)-(4a): $[a]D^{26}$+40.1 (neat) This indicates that racemization did not proceed and that it is possible to recover and reuse unreacted (R)-α-phenylethylamine.
Example 5: Preparation of (2S,2'RS,αR)-2-methyl-N-(2-methylbutyl)-N-(α-phenylethyl)butanamide: (2S,2'RS,αR)-(3a) (a 50:50 mixture of (2S,2'R,αR)-(3a) and (2S,2'S,αR)-(3a), Ar=Ph in the general formula (3))

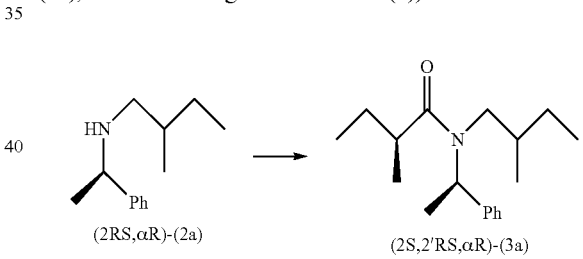

The procedures of Example 2 were repeated with the exception that 14.0 g of (2RS,αR)-(2a) obtained in Example 4 was used instead of (2S,αR)-(2a) obtained in Example 1 and used in Example 2 and that 7.10 g of (S)-2-butanoic acid (98.9% S, 97.9% ee) was used, so that obtained was 13.35 g of the target compound (2S,2'RS,αR)-(3a) (96.4% GC, yield 67%; total yield of fractions 70%).
(2S,2'RS,αR)-2-Methyl-N-(2-methylbutyl)-N-(α-phenylethyl)butanamide: (2S,2'RS,αR)-(3a) (a 50:50 mixture of (2S,2'R,αR)-(3a) and (2S,2'S,αR)-(3a)): $C_{18}H_{29}NO$

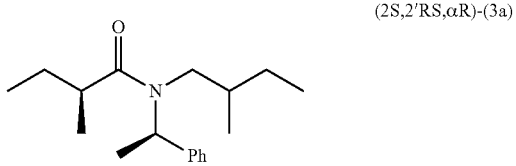 [SMILES: CCC(C)CN(C(=O)[C@@H](C)CC)[C@H](C)c1ccccc1]

Colorless oil.
Specific rotation: $[\alpha]D^{26}$+97.3 (c=1.0, CHC$_3$).

IR (D-ATR): ν=3063, 3030, 2964, 2933, 2874, 1639, 1496, 1463, 1418, 1380, 1271, 1231, 1207, 1186, 1156, 1119, 1089, 1049, 1028, 968, 912, 787, 758, 699 cm$^{-1}$.

$^1$H-NMR (600 MHz, CDC$_3$): δ=0.65-0.82 (6H, m), 0.86-0.92 (3H, m), 0.97-1.35 (~6H, m), 1.37-1.48 (1H, m), 1.56 (3×0.55H, br.d, J=~7 Hz), 1.65 (3×0.45H, d, J=~7 Hz), 1.72-1.84 (-1H, m), 2.57-2.66 (0.55H, m), 2.66-2.73 (0.45H, m), 2.84-3.07 (1.55H, m), 3.17-3.27 (0.45H, m), 5.11-5.21 (0.45H, m), 5.79-5.93 (0.55H, 2×q-like, J=7.0 Hz), 7.21-7.37 (5H, m) ppm.

In the $^1$H-NMR, observed were the severely overlapped spectra derived from four diastereomers including the diastereomers at position 2' and the diastereomers that result from the asymmetric nitrogen atom and are present at a ratio of ~55:45, and it was impossible to assign completely peaks. However, the spectra of two of these four diastereomers well matched with the spectrum of (2S,2'S,αR)-2-methyl-N-(2-methylbutyl)-N-(α-phenylethyl)butanamide observed in Example 2. The remaining two diastereomers are derived from (2S,2'R,αR)-2-methyl-N-(2-methylbutyl)-N-(α-phenylethyl)butanamide.

$^{13}$C-NMR (150 MHz, CDC13): δ=11.619, 11.623, 11.70, 11.74, 12.12, 12.21, 12.38, 12.40, 16.83, 17.066, 17.070, 17.16, 17.22, 17.45, 17.63, 17.75, 18.25, 18.30, 19.38, 19.39, 27.08, 27.26, 27.48, 27.55, 27.582, 27.584, 27.670, 27.673, 34.05, 34.60, 35.18, 35.26, 37.83, 37.96, 38.53, 38.54, 49.37, 49.81, 50.37, 50.54, 52.45, 52.57, 55.32, 55.40, 126.93, 127.01, 127.27, 127.28, 127.54, 127.57, 127.84, 127.90, 128.35, 128.37, 128.69, 128.70, 141.53, 141.54, 141.58, 141.64, 177.76, 177.80, 178.13, 178.14 ppm.

In the $^{13}$C-NMR spectrum, signals assigned to two diastereomers of (2S,2'S,αR)-2-methyl-N-(2-methylbutyl)-N-(α-phenylethyl)butanamide among the four diastereomers are shown with underlines, and signals assigned to two diastereomers of (2S,2'R,αR)-2-methyl-N-(2-methylbutyl)-N-(α-phenylethyl)butanamide are shown without underlines.

GC-MS (EI, 70 eV): 41, 57, 79, 105 (base peak), 120, 134, 156, 177, 204, 218, 275 (M$^+$).

Example 6: Preparation of (2S,2'RS)-2-methyl-N-(2-methylbutyl)butanamide: (2S,2'RS)-(1) (a 50:50 mixture of (2S,2'R)-(1) and (2S,2'S)-(1))

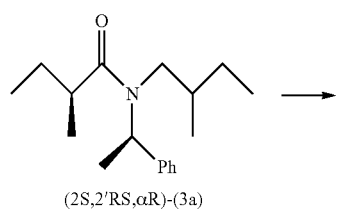

(2S,2'RS,αR)-(3a)

A mixture of 1.00 g of (2S,2'RS,αR)-2-methyl-N-(2-methylbutyl)-N-(α-phenylethyl)butanamide obtained in Example 5 and 35 ml of formic acid was stirred in a nitrogen atmosphere at 50 to 60° C. for 5 hours and then at room temperature for 16 hours. The reaction mixture was diluted with tert-butyl methyl ether, subjected to aftertreatment, i.e., washing, drying, and concentration, and then purified by silica gel column chromatography to obtain 0.54 g of the target compound (2S,2'RS)-(1) (99.8% GC, yield 90%).

(2S,2'RS)-2-Methyl-N-(2-methylbutyl)butanamide: (2S,2'RS)-(1) (a 50:50 mixture of (2S,2'R)-(1) and (2S,2'S)-(1)): C$_{10}$H$_{21}$NO

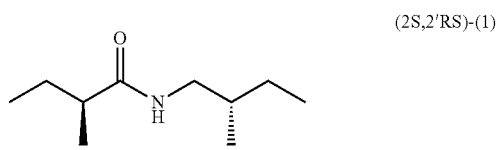

(2S,2'RS)-(1)

Colorless oil.

Specific rotation: [α]D$^{23}$+19.5 (c=3.3, CH$_3$CH$_2$OCH$_2$CH$_3$).

IR (D-ATR): ν=3296, 3089, 2963, 2931, 2876, 1645, 1553, 1462, 1381, 1269, 1236, 1108, 968, 766, 704 cm$^{-1}$.

$^1$H-NMR (600 MHz, CDCl$_3$): δ=0.87-0.93 (9H, m), 1.12-1.19 (1H, m), 1.13 (3H, d, J=6.9 Hz), 1.34-1.46 (2H, m), 1.50-1.59 (1H, m), 1.62-1.70 (1H, m), 2.05-2.13 (1H, m), 3.04 (0.5H, dt-like, J=~13.4, —7 Hz), 3.09 (0.5H, dt-like, J=~13.4, —6.5 Hz), 3.17 (0.5H, dt-like, J=~13.4, —6.0 Hz), 3.23 (0.5H, dt-like, J=~13.4, —7 Hz)5.48 (1H, NH, br.s) ppm.

$^{13}$C-NMR (150 MHz, CDCl$_3$): δ=11.40 (0.5C), 11.42 (0.5C), 12.11, 17.29 (0.5C), 17.31 (0.5C), 17.80, 27.15, 27.52, 35.10, 43.62, 45.01, 176.57 ppm. GC-MS (EI, 70 eV): 41, 57 (base peak), 71, 85, 102, 114, 128, 143, 156, 171 (M$^+$).

Chiral phase GC (in conditions identical to those in Example 3): 3.92% (Rt 17.51 min), 96.08% (Rt 17.97 min).

The configuration at position 2 was determined to be 96.1% S from the chiral phase GC. This demonstrates that this preparation process enables the preparation of the target compound in a high optical purity.

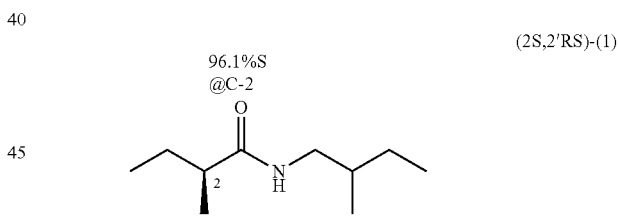

(2S,2'RS)-(1)

Preparation 1 of (2RS,2'RS)-2-methyl-N-(2'-methylbutyl)butanamide: (2RS,2'RS)-(1)

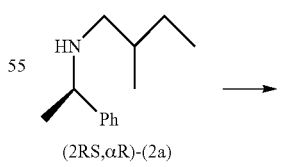

(2S,2'RS)-(1)

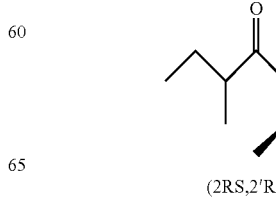

(2RS,αR)-(2a)

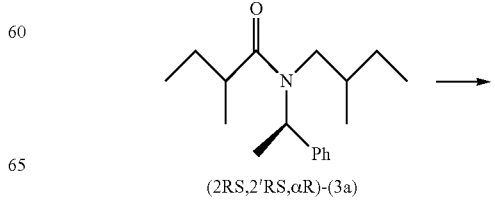

(2RS,2'RS,αR)-(3a)

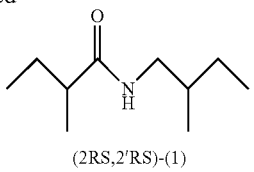

(2RS,2'RS)-(1)

Example 7: Preparation of (2RS,2'RS)-2-methyl-N-(2-methylbutyl)butanamide: (2RS,2'RS)-(1) (a 25:25:25:25 mixture of (2R,2'R)-(1), (2R,2'S)-(1), (2S,2'R)-(1), and (2S,2'S)-(1))

To an ice-cooled mixture of 0.50 g of (±)-2-butanoic acid, 1.20 g of 1-methylimidazole, and 20 ml of acetonitrile was added 1.44 g of diphenylphosphoryl chloride in a nitrogen atmosphere with stirring at room temperature. After the mixture was stirred at room temperature for 3.5 hours, 0.93 g of (2RS,αR)-2-methylbutyl-α-phenylethylamine obtained in Example 1 was added with water-cooling, and the mixture was stirred at 90 to 95° C. for 36 hours. The reaction mixture was diluted with tert-butyl methyl ether, and the resulting solution was washed, dried, and concentrated to obtain 1.21 g of the crude target compound (2RS,2'RS,αR)-(3a) (90.9% GC, yield 82%).

The procedures of Example 3 were repeated with the exception that 1.21 g of the resulting crude product (2RS,2'RS,αR)-(3a) was used instead of (2S,2'S,αR)-2-methyl-N-(2-methylbutyl)-N-(α-phenylethyl)butanamide used in Example 3, so that obtained was 0.745 g of the target compound (2RS,2'RS)-(1) (99.4 to 100% GC, yield 99%).

(2RS,2'RS)-2-Methyl-N-(2-methylbutyl)butanamide: (2RS,2'RS)-(1) (a ~25:25:25: 25 mixture of (2R,2'R)-(1), (2R,2'S)-(1), (2S,2'R)-(1), and (2S,2'S)-(1)): C₁₀H₂₁NO

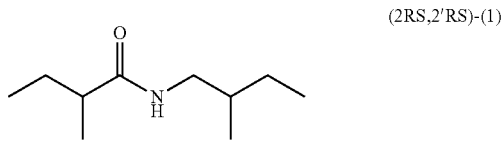

(2RS,2'RS)-(1)

Colorless oil.

Various spectra of this compound were the same as those of (2S,2'RS)-2-methyl-N-(2-methylbutyl)butanamide: (2S,2'RS)-(1) determined in Example 6.

The ¹H-NMR signals derived from hydrogen atoms at position 1' were observed at δ=3.04 (0.5H, dt-like, J=~13.4, —7 Hz), 3.09 (0.5H, dt-like, J=~13.4, ~6.5 Hz), 3.17 (0.5H, dt-like, J=to 13.4, ~6.0 Hz), and 3.23 (0.5H, dt-like, J=~13.4, —7 Hz) ppm. Decoupling of the signal NH: δ=5.48 (br. s) ppm caused separated signals to be observed at δ=3.04 (0.5H, dd, J=13.4, 7.3 Hz), 3.09 (0.5H, dd, J=13.4, 7.2 Hz), 3.18 (0.5H, dd, J=13.4, 6.1 Hz), and 3.23 (0.5H, dd, J=13.4, 6.1 Hz) ppm and allowed observation of the signal as non-overlapping peaks. Among these peaks, the peaks observed at δ=3.04 and 3.23 were assigned to the diastereomer (2R*,2'R*)-(1) (i.e., (2R,2'R)-(1) and (2S,2'S)-(1)), and the peaks observed at δ=3.09 and 3.18 were assigned to the diastereomer (2R*,2'S*)-(1) ((2R,2'S)-(1) and (2S,2'R)-(1)). This demonstrates that the diastereomer ratio of [(2R,2'R) +(2S,2'S)] : [(2R,2'S) +(2S,2'R)] can be determined from ¹H-NMR. For example, this process was used to determine the purity of isomers in Example 3.

Chiral phase GC: HP 7890B, Column: Cyclosil-B 30 m×0.25 mmφ×0.25 µm, 116° C. +0.4° C./min const., carrier gas: He 1 mL/min, Inj: 200° C., detector: FID 230° C.: 49.90% (Rt 37.70 min), 50.10% (Rt 38.01 min). The peaks derived from the configuration at position 2 was separated into 1:1. This demonstrates that the diastereomer ratio of [(2S,2'S)+(2S,2'R)] : [(2R,2'R) +(2R,2'S)] can be determined. For example, this process was used to determine the purity of isomers in Examples 3 and 6.

Preparation 2 of (2RS,2'RS)-2-methyl-N-(2'-methylbutyl)butanamide: (2RS,2'RS)-(1)

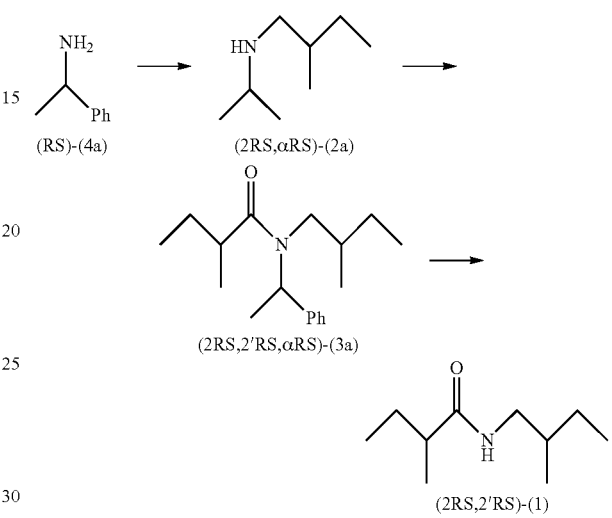

Example 8: Preparation of (2RS,2'RS)-2-methyl-N-(2-methylbutyl)butanamide: (2RS,2'RS)-(1) (a ~25:25:25:25 mixture of (2R,2'R)-(1), (2R,2'S)-(1), (2S,2'R)-(1), and (2S,2'S)-(1))

A mixture of 1,201.29 g of (±)-α-phenylethylamine (98.51% GC) and 882.36 g of (±)-2-methylbutyl p-toluenesulfonate (89.40% GC; containing 9.7% toluene) was stirred at 85° C. for 62 hours in a nitrogen atmosphere. The reaction mixture was cooled and then diluted with toluene. The diluted mixture was subjected to aftertreatment, i.e., washing, drying, and concentration and then distilled at a reduced pressure to obtain 543.05 g of the intermediate (2RS,αRS)-(2a) (99.29% GC, yield 87%, total yield of fractions 95%).

(2RS,αRS)-2-methylbutyl-α-phenylethylamine: (2RS,αRS)-(2a): a ~25:25:25:25 mixture of (2R,αR)-(2a), (2R,αS)-(2a), (2S,αR)-(2a), and (2S,αS)-(2a), Ar=Ph in the general formula (2)): C₁₃H₂₁N

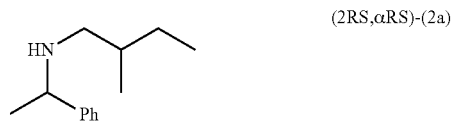

(2RS,αRS)-(2a)

Colorless oil.

Boiling point: 108° C./0.2 kPa.

Various spectra of this compound were the same as those of (2RS,αR)-2-methylbutyl-α-phenylethylamine: (2RS,αR)-(2a) determined in Example 4.

A mixture of 538.11 g of (2RS,αRS)-(2a) thus prepared, 704.15 g of pyridine, and 270 g of tetrahydrofuran was cooled with ice in a nitrogen atmosphere, and 503.18 g of (±)-2-methylbutyryl chloride was added dropwise at 15° C. or lower with stirring. The reaction mixture was heated and then stirred at 55° C. for 15 hours. The reaction mixture was cooled, followed by addition of water and extraction with toluene. The organic layer was subjected to aftertreatment, i.e., washing, drying, and concentration and then concentrated at a reduced pressure to obtain 783.89 g of the crude intermediate (2RS,2'RS,aRS)-(3a) (98.22% GC, quantitative yield).

A mixture of 783.52 g of the crude product (2RS,2'RS, αRS)-(3a), 0.78 g of 4-tert-butylcatechol, and 3,858 g of formic acid was stirred at 60° C. for 24 hours in a nitrogen atmosphere. After cooled, the reaction mixture was diluted with toluene, subjected to aftertreatment, i.e., washing, drying, and concentration, and then distilled at a reduced pressure to obtain 345.3 g of the target compound (2RS, 2'RS)-(1) (99.52% GC, yield 73%, total yield of fractions 85%).

(2RS,2'RS)-2-Methyl-N-(2-methylbutyl)butanamide: (2RS,2'RS)-(1) (a ~25:25:25: 25 mixture of (2R,2'R)-(1), (2R,2'S)-(1), (2S,2'R)-(1), and (2S,2'S)-(1)): $C_{10}H_{21}NO$

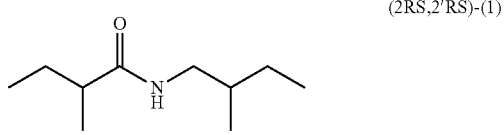

(2RS,2'RS)-(1)

Colorless oil.
Boiling point: 110 to 113° C./0.1 kPa.
Various spectra of this compound were the same as those of (2S,2'RS)-2-methyl-N-(2-methylbutyl)butanamide: (2S, 2'RS)-(1) determined in Example 6.

Preparation of (2RS,2'S)-2-methyl-N-(2'-methylbutyl)butanamide: (2RS,2'S)-(1) (a 50:50 mixture of (2RS,2'S)-(1) and (2RS,2'S)-(1))

Example 9: Preparation of (2RS,2'S)-2-methyl-N-(2-methylbutyl)butanamide: (2RS,2'S)-(1) (a 50:50 mixture of (2R,2'S)-(1) and (2S,2'S)-(1))

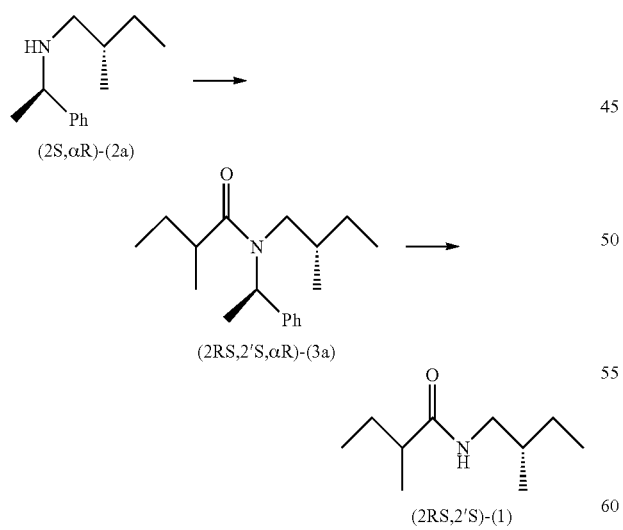

The procedures of Example 2 were repeated with the exception that (±)-2-butanoic acid was used instead of (S)-2-butanoic acid used in Example 2, so that a crude product (2RS,2'S,αR)-(3a) was obtained from 5.06 g of (2S,αR)-(2a) obtained in Example 1. The procedures of Example 3 were then repeated with the exception that this crude product (2RS,2'S,αR)-(3a) was used instead of (2S, 2'S,αR)-(3a) used in Example 3, so that obtained was 2.20 g of the target compound (2RS,2'S)-(1) (99.4% GC, yield 70% in 2 steps).

(2RS,2'S)-2-Methyl-N-(2-methylbutyl)butanamide: (2RS,2'S)-(1) (a 50:50 mixture of (2R,2'S)-(1) and (2S,2'S)-(1)): $C_{10}H_{21}NO$

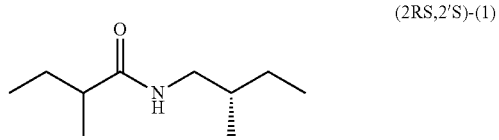

(2RS,2'S)-(1)

Colorless oil.
Specific rotation: $[\alpha]D^{26}+4.83$ (c=3.0, $CH_3CH_2OCH_2CH_3$).
Various spectra of this compound were the same as those of (2S,2'RS)-2-methylbutyl-α-phenylethylamine: (2S,2'RS)-(1) determined in Example 6.

The configuration at position 2' was estimated to be ~97% S because this compound was prepared in steps similar to those as described in Examples 1 to 3.

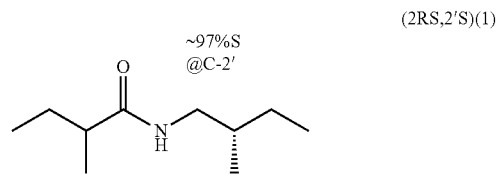

(2RS,2'S)(1)

Example 10: Preparation of (2S,αS)-2-methylbutyl-α-phenylethylamine: (2S,αS)-(2a) (Ar=Ph in the general formula (2))

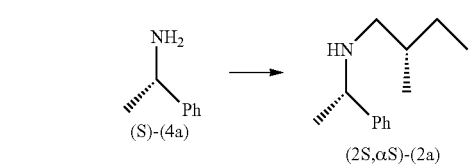

A mixture of 1.60 g of (S)-2-methylbutyl bromide and 3.85 g of (S)-α-phenylethylamine (~100% ee) was stirred at 80 to 85° C. for 15 hours in a nitrogen atmosphere. The reaction mixture was cooled, and an aqueous 5% sodium hydroxide solution was added. The organic layer was separated, and the aqueous layer was subjected to extraction with tert-butyl methyl ether. The combined organic layers was concentrated, and the concentrate was purified by silica gel column chromatography to obtain 1.44 g of the target compound (2S,αR)-(2a) (~99.6% GC, yield 70%).

(2S,αS)-2-Methylbutyl-α-phenylethylamine: (2S,αS)-(2a): $C_{13}H_{21}N$

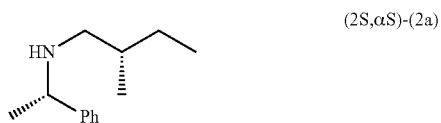

(2S,αS)-(2a)

Colorless oil.

Specific rotation: $[\alpha]_D^{24}$-56.6 (c=1.01, CHCl$_3$).

IR (D-ATR): ν=3063, 3026, 2960, 2926, 2874, 2810, 1603, 1493, 1452, 1369, 1351, 1304, 1229, 1211, 1127, 1028, 760, 700 cm$^{-1}$. $^1$H-NMR (600 MHz, CDCl$_3$): δ=0.84 (3H, t, J=7.4 Hz), 1.05-1.13 (1H, m), ~1.10-1.40 (1H, NH, br.), 1.34 (3H, d, J=6.6 Hz), 1.39-1.46 (1H, m), 1.46-1.52 (1H, m), 2.31 (1H, dd, J=11.5, 6.5 Hz), 2.33 (1H, dd, J=11.5, 6.5 Hz), 3.72 (3H, q, J=6.6 Hz), 7.21-7.26 (1H, m), 7.30-7.34 (4H, m) ppm. The ratio of the diastereomers resulting from the stereochemical configuration at position 2 was estimated to be 2S:2R=96.6:3.4 by calculation from the integrated areas under the peaks derived from two diastereotopic hydrogen atoms at position 1 (two sets of dd per the single diastereomer) in a manner similar to that described above.

$^{13}$C-NMR (150 MHz, CDCl$_3$): δ=11.34, 17.82, 24.67, 27.42, 35.15, 54.15, 58.62, 126.71 (2C), 126.85, 128.47 (2C), 146.31 ppm.

GC-MS (EI, 70 eV): 41, 51, 65, 77, 91, 105 (base peak), 118, 134, 176, 191 (M$^+$).

Example 11: Preparation of (2RS,αS)-2-methylbutyl-α-phenylethylamine: (2RS,αS)-(2a) (a 50:50 mixture of (2R,αS)-(2a) and (2S,αS)-(2a), Ar=Ph in the general formula (2))

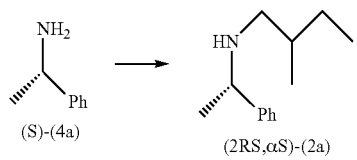

The procedures of Example 1 were repeated with the exception that 132 g of (±)-2-methylbutyl p-toluenesulfonate was used instead of (S)-2-methylbutyl p-toluenesulfonate used in Example 1, and 170 g of (S)-α-phenylethylamine was used instead of (R)-α-phenylethylamine used in Example 1, so that obtained was 96.3 g of the target compound (2RS,αS)-(2a) (99.2 to 99.6% GC, total yield of fractions 90%).

(2RS,αS)-2-Methylbutyl-α-phenylethylamine: (2RS,αS)-(2a): C$_{13}$H$_{21}$N

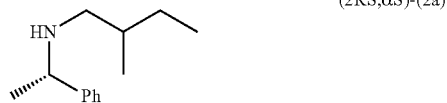

Colorless oil.

Boiling point: 66 to 69° C./0.5 kPa.

Specific rotation: $[\alpha]_D^{26}$-61.4 (c=1.0, CHCl$_3$).

Various spectra of this compound were the same as those of (2RS,2'R)-2-methylbutyl-α-phenylethylamine: (2RS, 2'R)-(2a) determined in Example 4.

Example 12: Preparation of (2S,αS)-2-methylbutyl-α-1-naphthylethylamine: (2S, αS)-(2b) (Ar=Np=1-naphthyl in the general formula (2))

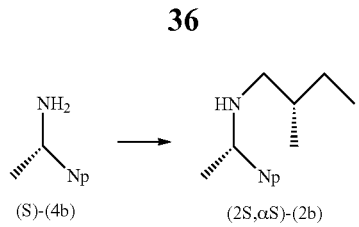

wherein Np represents a 1-naphthyl group (hereinafter the same shall apply).

A mixture of 1.30 g of (S)-2-methylbutyl bromide and 4.41 g of (S)-α-naphthylethylamine (~100 ee) was stirred at 70 to 80° C. for 24 hours in a nitrogen atmosphere. The reaction mixture was cooled, and an aqueous 5% sodium hydroxide solution was added. The organic layer was separated, and the aqueous layer was subjected to extraction with tert-butyl methyl ether. The combined organic layers was concentrated, and the concentrate was purified by silica gel column chromatography to obtain 1.66 g of the target compound (2S,αS)-(2b) (~99.7% GC, yield 79%).

(2S,αS)-2-Methylbutyl-α-1-naphthylethylamine: (2S,αS)-(2b):C$_{17}$H$_{23}$N

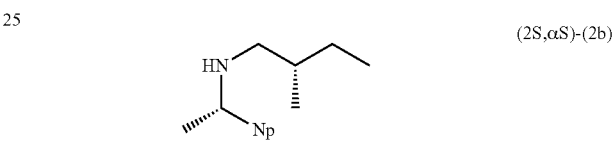

Colorless oil.

Specific rotation: $[\alpha]_D^{24}$-50.1 (c=1.03, CHCl$_3$).

IR (D-ATR): ν=3049, 2960, 2925, 2873, 2813, 1596, 15101, 1461, 1394, 1377, 1130, 799, 778 cm$^{-1}$.

$^1$H-NMR (600 MHz, CDCl$_3$): δ=0.87 (3H, t, J=7.3 Hz), 0.90 (3H, d, J=6.7 Hz), 1.09-1.18 (1H, m), 1.25-1.55 (1H, NH, broad), 1.44-1.51 (1H, m), 1.49 (3H, d, J=6.6 Hz), 1.51-1.58 (1H, m), 2.42 (1H, dd, J=11.5, 6.5 Hz), 2.46 (1H, dd, J=11.5, 6.6 Hz), 4.60 (1H, q, J=6.6 Hz), 7.46-7.53 (3H, m), 7.68 (1H, br.d, J=7.1 Hz), 7.74 (1H, br.d, J=8.1 Hz), 7.87 (1H, br.d, J=7.9 Hz), 8.21 (1H, br.d, J=8.4 Hz) ppm.

The ratio of the diastereomers resulting from the stereochemical configuration at position 2 was estimated to be major:minor=(2S,αS):(2R,αS)=98.06:1.94 from the $^1$H-NMR. $^{13}$C-NMR (150 MHz, CDCl$_3$): δ=11.40, 17.89, 23.84, 27.47, 35.39, 54.06, 54.38, 122.84, 123.17, 125.35, 125.77, 125.86, 127.14, 129.07, 131.51, 134.10, 141.74 ppm.

Example 13: Preparation of (2RS,αR)-2-methylbutyl-α-1-naphthylethylamine: (2RS,αR)-(2b) (which is a 50:50 mixture of (2R,αR)-(2b) and (2S,αR)-(2b), in a case where Ar=Np=1-naphthyl in the general formula (2))

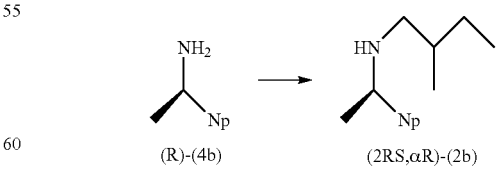

In a nitrogen atmosphere, 8.94 g of (±)-2-methylbutyl p-toluenesulfonate and 20.0 g of (R)-α-1-naphthylethylamine were stirred at 70° C. for 25 hours. After cooled, the reaction mixture was diluted with tert-butyl methyl ether, and the diluted solution was subjected to aftertreatment, i.e., washing, drying, and concentration to obtain 26.22 g of a crude product (31.4% GC). This crude product (8.08 g) was purified by silica gel column chromatography to obtain 2.61 g of the target compound (2RS,αR)-(2b) (94.5 to 96.7% GC, yield 98%).

(2RS,αR)-2-Methylbutyl-α-1-naphthylethylamine: (2RS, αR)-(2b) (a 50:50 mixture of (2R,αR)-(2b) and (2S,αR)-(2b)): $C_{17}H_{23}N$

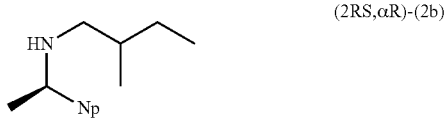
(2RS,αR)-(2b)

Colorless oil.

IR (D-ATR): ν=3048, 2959, 2925, 2873, 1596, 1510, 1461, 1394, 1376, 1130, 799, 778 cm$^{-1}$.

$^{H\text{-}NMR}$ (600 MHz, CDCl$_3$): ν=0.852 (3×0.5H, t, J=7.4 Hz), 0.865 (3×0.5H, t, J=7.4 Hz), 0.90 (3×0.5H, d, J=6.7 Hz), 0.93 (3×0.5H, d, J=6.6 Hz), 1.09-1.18 (1H, m), 1.35-1.55 (1H, NH, br.), 1.39 (0.5H, ddq, J=~13.2, 5.5, 7.4 Hz), 1.44-1.50 (0.5H, m), 1.490 (3×0.5H, d, J=6.6 Hz), 1.493 (3×0.5H, d, J=6.6 Hz), 1.49-1.57 (1H, m), 2.32 (0.5H, dd, J=11.4, 7.6 Hz), 2.42 (0.5H, dd, J=11.5, 6.5 Hz), 2.46 (0.5H, dd, J=11.5, 6.5 Hz), 2.55 (0.5H, dd, J=11.5, 5.5 Hz), 4.60 (1H, q, J=6.5 Hz), 7.45-7.53 (3H, m), 7.68 (1H, br.dd, J=7.0, 3.9 Hz), 7.75 (1H, br.d, J=8.1 Hz), 7.88 (1H, br.d, J=8.2 Hz), 8.21 (1H, br.d, J=8.4 Hz) ppm. $^{13}$C-NMR (150 MHz, CDCl$_3$): δ=11.40 (0.5C), 11.54 (0.5C), 17.89 (0.5C), 17.95 (0.5C), 23.84 (0.5C), 23.89 (0.5C), 27.47 (0.5C), 27.80 (0.5C), 35.40 (0.5C), 35.46 (0.5C), 54.06, 54.38, 122.84, 123.17, 125.36, 125.77, 125.86, 127.14, 129.07, 131.51, 134.10, 141.74 ppm.

GC-MS (EU 70 eV): 29, 41, 57, 77, 92, 115, 129, 141, 155 (base peak), 168, 184, 226, 241 (M$^+$).

Example 14: Resolution of diastereomers of (2RS,αR)-2-methylbutyl-α-1-naphthylethylamine: (2RS,αR)-(2b)

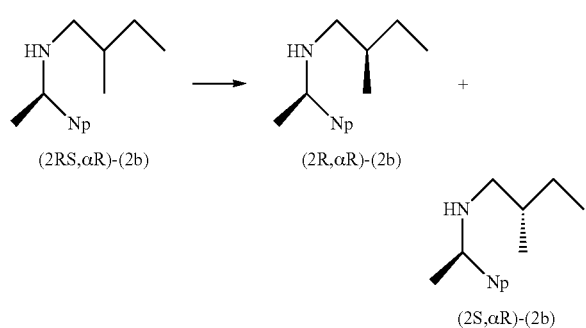

The mixtures, (2RS,αR)-2-Methylbutyl-α-1-naphthylethylamine: (2RS,αR)-(2b) obtained in Example 13, were separated by high-performance liquid chromatography (HPLC).

HPLC conditions:Thermo Fisher Scientific UltiMate-3000, Column: BEH C18 (2.1×100 mm×1.7 μm; 30° C., Elution: C$_2$H$_5$OH:CH$_3$H$_5$OH:CH$_3$OH: 10 mM NH$_4$OCOCH$_3$ aq=10:10:20:60; 0.2 ml/min, Detector: UV 210 nm. This compound was eluted at Rt=21.113 and 22.007 min, resulting in resolution R=1.524. The resolution R is defined as follows:

R=(t$_{R2}$-t$_{R1}$)/[(W$_1$+W$_2$)÷2]
R: resolution

W$_n$: peak width of component n t$_{Rn}$: retention time of component n A resolution R of 1.5 or higher indicates complete resolution.

The following two fractions were obtained by preparative HPLC in the conditions as described above.

(2R,αR)-2-Methylbutyl-α-1-naphthylethylamine: (2R, αR)-(2b): $C_{17}H_{23}N$

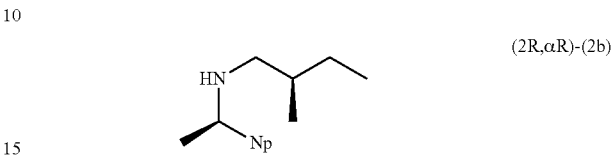
(2R,αR)-(2b)

HPLC retention time: Rt=21.113 min.

Colorless oil.

Specific rotation: [α]D$^{23}$+48.1 (c=1.02, CHCl$_3$).

Various spectra of this fraction were the same as those of (2S,αS)-2-methylbutyl-1-naphthylethylamine: (2S,αS)-(2b), which is an enantiomer of (2R,αR)-2-methylbutyl-α-1-naphthylethylamine, determined in Example 12.

The ratio of the diastereomers resulting from the stereochemical configuration at position 2 was estimated to be major:minor=(2R,αR):(2S,αR)=97.08:2.92 from the $^1$H-NMR. (2S,αR)-2-Methylbutyl-α-1-naphthylethylamine: (2S,αR)-(2b): $C_{17}H_{23}N$

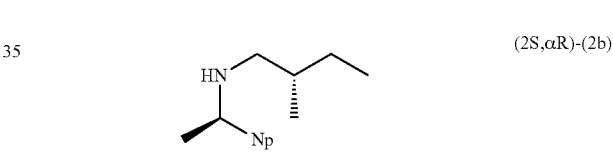
(2S,αR)-(2b)

HPLC retention time: Rt=21.113 min

Colorless oil.

Specific rotation: [α]D$^{25}$+59.3 (c=1.01, CHCl$_3$).

IR (D-ATR): ν=3048, 2960, 2925, 2873, 1596, 1511, 1462, 1394, 1376, 1130, 799, 778 cm$^{-1}$.

(600 MHz, CDCl$_3$): δ=0.85 (3H, t, J=7.4 Hz), 0.93 (3H, d, J=6.7 Hz), 1.09-1.18 (1H, m), 1.35-1.65 (1H, NH, broad), 1.35-1.43 (1H, m), 1.50 (3H, d, J=6.6 Hz), 1.51-1.58 (1H, m), 2.32 (1H, dd, J=11.4, 7.6 Hz), 2.56 (1H, dd, J=11.4, 5.5 Hz), 4.60 (1H, q, J=6.6 Hz), 7.45-7.53 (3H, m), 7.68 (1H, br.d, J=7.1 Hz), 7.75 (1H, br.d, J=8.4 Hz), 7.88 (1H, br.d, J=7.9 Hz), 8.21 (1H, br.d, J=8.4 Hz) ppm.

The ratio of the diastereomers resulting from the stereochemical configuration at position 2 was estimated to be major:minor=(2S,αR):(2R,αR)=98.54: 1.46 from the $^1$H-NMR.

$^{13}$C-NMR (150 MHz, CDCl$_3$): δ=11.54, 17.95, 23.86, 27.80, 35.42, 54.05, 54.37, 122.86, 123.15, 125.37, 125.80, 125.86, 127.17, 129.07, 131.51, 134.10, 141.65 ppm.

Example 15: Preparation of (2S,αRS)-2-methylbutyl-α-2,4-dichlorophenylethylamine: (2S,αRS)-(2c) (a 50:50 mixture of (2S,αR)-(2c) and (2S,αS)-(2c), Ar=2,4-dichlorophenyl in the general formula (2))

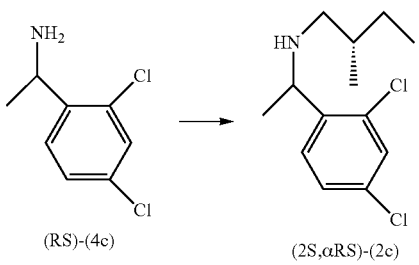

(RS)-(4c) → (2S,αRS)-(2c)

A mixture of 5.70 g of (S)-2-methylbutyl p-toluenesulfonate and 10.0 g of α-dichlorophenylethylamine was stirred at 70° C. for 10 hours in a nitrogen atmosphere. The reaction mixture was cooled, and an aqueous 25% sodium hydroxide solution was added. The organic layer was separated and subjected to aftertreatment, i.e., washing, drying, and concentration, and the concentrate was purified by silica gel column chromatography to obtain 4.20 g of the target compound (81.7 to 97.0% GC, yield 91%).

(2S,αRS)-2-Methylbutyl-α-2,4-dichlorophenylethylamine: (2S,αRS)-(2c) (a 50:50 mixture of (2S,αR)-(2c) and (2S,αS)-(2c))]:C$_{13}$H$_{19}$Cl$_2$N

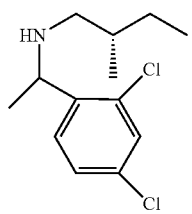

(2S,αRS)-(2c)

Colorless oil.
IR (D-ATR): ν=2961, 2927, 2874, 2814, 1588, 1560, 1464, 1380, 1370, 1342, 1135, 1101, 1068, 1046, 865, 816, 692, 571 cm$^{-1}$.
$^1$H-NMR (500 MHz, CDCl$_3$): δ=0.847 (3×0.5H, t, J=7.6 Hz), 0.851 (3×0.5H, t, J=7.3 Hz), 0.87 (3×0.5H, d, J=6.5 Hz), 0.89 (3×0.5H, d, J=6.5 Hz), 1.05-1.17 (1H, m), 1.15-1.35 (1H, NH, broad), 1.290 (3×0.5H, d, J=6.5 Hz), 1.292 (3×0.5H, d, J=6.5 Hz), 1.30-1.39 (0.5H, m), 1.39-1.53 (1.5H, m), 2.12 (0.5H, dd, J=11.4, 7.6 Hz), 2.25 (0.5H, dd, J=11.5, 6.5 Hz), 2.31 (0.5H, dd, J=11.5, 6.1 Hz), 2.43 (0.5H, dd, J=11.5, 5.4 Hz), 4.178 (0.5H, q, J=6.5 Hz), 4.180 (0.5H, q, J=6.5 Hz), 7.24 (1H, dd, J=8.4, 1.9 Hz), 7.33 (1H, d, J=2.3 Hz), 7.49 (1H, dd, J=8.4, 2.3 Hz) ppm. $^{13}$C-NMR (125 MHz, CDCl$_3$): δ=11.21 (0.5C), 11.38 (0.5C), 17.63 (0.5C), 17.70 (0.5C), 22.76 (0.5C), 22.80 (0.5C), 27.22 (0.5C), 27.55 (0.5C), 35.10 (0.5C), 35.12 (0.5C), 53.80 (0.5C), 53.85 (0.5C), 54.02 (0.5C), 54.09 (0.5C), 127.34 (0.5C), 128.43 (0.5C), 128.46 (0.5C), 129.12, 132.45, 133.73, 141.70 ppm. GC-MS (EI, 70 eV): 30, 41, 57, 75, 102, 117, 137, 152, 173 (base peak), 202, 244, 244, 259 (M$^+$).

The α-arylethyl-2-methylbutylamine compounds (2b) and (2c) obtained in Examples 12, 13, 14, and 15 can be used to prepare 2-methyl-N-(2'-methylbutyl)butanamide (1).
Comparative Examples of preparation processes: Attempts of preparation of 2-methyl-N-(2'-methylbutyl)butanamide using a benzyl group instead of an α-arylethyl group used in the present invention

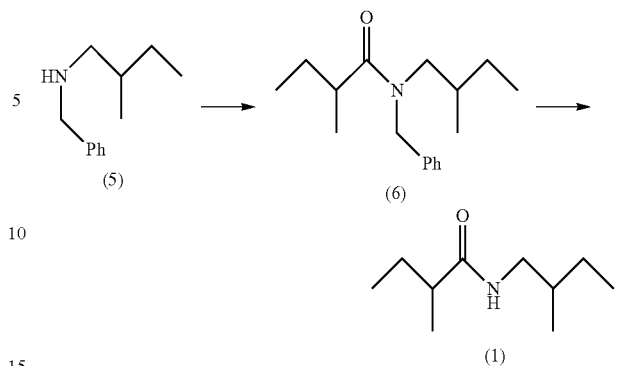

(5) → (6) → (1)

Comparative Example 1: Preparation of (2S,2'S)-N-benzyl-2-methyl-N-(2'-methylbutyl)butanamide: (2S,2'S)-(6)

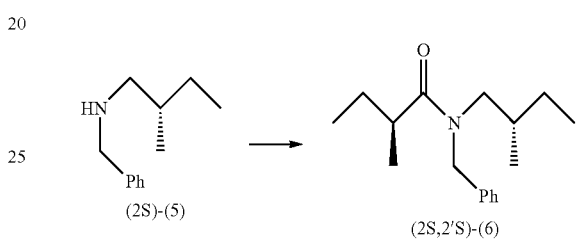

(2S)-(5) → (2S,2'S)-(6)

To an ice-cooled mixture of 2.00 g of (S)-2-methylbutanoic acid (98.45% S, 96.9% ee), 5.95 g of triethylamine, and 12 ml of tetrahydrofuran was added 5.27 g of diphenylphosphoryl chloride in a nitrogen atmosphere. The mixture was stirred under cooling with ice for 1 hour and then at room temperature for 30 minutes. The resulting crystals were filtered off through celite, and the cake was washed with 20 ml of tetrahydrofuran to obtain a mixed acid anhydride as a filtrate. The mixed acid anhydride solution was added to a mixture of 3.65 g of (S)-benzyl-2-methylbutylamine and 20 ml of tetrahydrofuran with stirring under ice-cooling. The reaction mixture was stirred at room temperature for 18 hours, poured into dilute hydrochloric acid, and then subjected to extraction with ethyl acetate. The organic layer was subjected to aftertreatment, i.e., washing, drying, and concentration, and the concentrate was purified by silica gel column chromatography to obtain 3.12 g of the target compound (~100% GC, yield 67%).

(2S,2'S)-N-Benzyl-2-methyl-N-(2'-methylbutyl)butanamide: (2S,2'S)-(6): C$_{17}$H$_{27}$NO

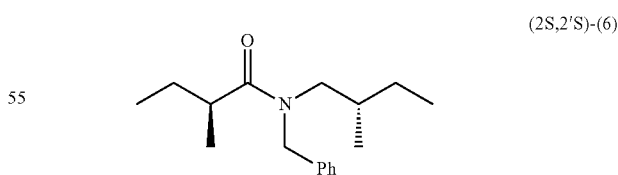

(2S,2'S)-(6)

Colorless liquid
Specific rotation: [α]D$^{27}$+26.1 (c=2.0, CH$_3$CH$_2$OCH$_2$CH$_3$). IR (D-ATR): ν=3064, 3030, 2963, 2931, 2875, 1645, 1496, 1464, 1454, 1425, 1380, 1264, 1216, 1121, 1078, 1029, 1000, 966, 729, 698 cm$^{-1}$.
$^1$H-NMR (600 MHz, CDCl$_3$): δ=0.84 (3×0.5H, t-like, J=~7.4 Hz), 0.86-0.93 (7.5H, m), 1.06-1.16 (1H, m), 1.08 (3×0.5H, d, J=6.7 Hz), 1.15 (3×0.5H, d, J=6.7 Hz), 1.33-1.51

(2H, m), 1.67-1.85 (2H, m), 2.53 (0.5H, hex, J=6.8 Hz), 2.67 (0.5H, hex, J=6.8 Hz), 3.03 (0.5H, dd, J=14.8, 8.3 Hz), 3.11 (0.5H, dd, J=14.8, 6.9 Hz), 3.26 (0.5H, dd, J=13.5, 7.0 Hz), 3.29 (0.5H, dd, J=13.5, 7.9 Hz), 4.52 (0.5H, d-like, J=~15 Hz)4.55 (0.5H, d-like, J=17 Hz), 4.62 (0.5H, d, J=17.2 Hz), 4.74 (0.5H, d, J=14.7 Hz), 7.13-7.17 (1H, d-like, J=7.39 Hz), 7.19-7.32 (3H, m), 7.35 (1H, t-like, J=-7.5 Hz) ppm. $^{13}$C-NMR (150 MHz, CDCl$_3$): δ=11.46 (0.5C), 11.59 (0.5C), 12.19 (0.5C), 12.20 (0.5C), 17.07 (0.5C), 17.12 (0.5C), 17.77 (0.5C), 17.95 (0.5C), 27.10 (0.5C), 27.25 (0.5C), 27.53 (0.5C), 27.60 (0.5C), 33.54 (0.5C), 34.45 (0.5C), 37.30 (0.5C), 37.78 (0.5C), 48.72 (0.5C), 51.53 (0.5C), 52.13 (0.5C), 52.60 (0.5C), 126.22, 127.23 (0.5C), 127.53 (0.5C), 128.08, 128.62, 128.94, 137.69 (0.5C), 138.29 (0.5C), 177.44 (0.5C), 177.68 (0.5C) ppm. Diastereomers resulting from the asymmetric carbon atoms at positions 2 and 2' and the asymmetric nitrogen atom of which inversion is difficult due to steric hindrance were present at a ratio of -50:50 in the $^1$H- and $^{13}$C-NMR samples in CDCl$_3$.

Comparative Example 2: Preparation of (2RS,2'S)-N-benzyl-2-methyl-N-(2'-methylbutyl)butanamide: (2RS,2'S)-(6) (a ~50:50 mixture of (2R,2'S)-(6) and (2S,2'S)-(6))

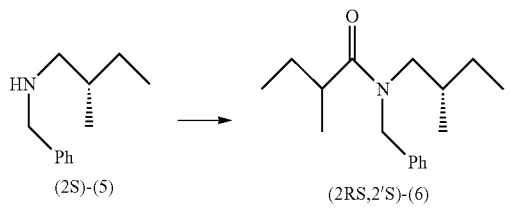 [SMILES: CC[C@H](C)CNCc1ccccc1 ; CCC(C)C(=O)N(Cc1ccccc1)C[C@@H](C)CC]

The procedures of Comparative Example 1 were repeated with the exception that (±)-2-methylbutanoic acid was used instead of (S)-2-methylbutanoic acid used in Comparative Example 1 and that 10.30 g of (S)-benzyl-2-methylbutylamine was used, so that obtained was 14.33 g of the target compound (2RS,2'S)-(6) (98.9% GC, yield 97%).

(2RS,2'S)-N-Benzyl-2-methyl-N-(2'-methylbutyl)butanamide: (2RS,2'S)-(6) (a ~50:50 mixture of (2R,2'S)-(6) and (2S,2'S)-(6)): C$_{17}$H$_{27}$NO Yellowish liquid Specific rotation: [α]D$^{27}$-0.73 (c=2.0, CH$_3$CH$_2$OCH$_2$CH$_3$).

IR (D-ATR): ν=3064, 3029, 2963, 2931, 2875, 1644, 1496, 1464, 1454, 1425, 1380, 1264, 1217, 1121, 1078, 1029, 1000, 966, 729, 698 cm$^{-1}$. $^1$H-NMR (600 MHz, CDCl$_3$): δ=0.84 (3×0.5H, t-like, J=~7.4 Hz), 0.86-0.93 (7.5H, m), 1.06-1.17 (4H, m), 1.33-1.50 (2H, m), 1.67-1.85 (2H, m), 2.49-2.57 (0.5H, m), 2.62-2.71 (0.5H, m), 2.96-3.06 (0.5H, m), 3.08-3.16 (0.5H, m), 3.17-3.23 (0.25H, m), 3.23-3.32 (0.5H, m), 3.32-3.39 (0.25H, m), 4.49-4.70 (1.75H, m), 4.75 (0.25H, d-like, J=~14.8 Hz), 7.15 (1H, d-like, J=7.39 Hz), 7.19-7.32 (3H, m), 7.35 (1H, t-like, J=~7.5 Hz) ppm. $^{13}$C-NMR (150 MHz, CDCl$_3$): δ=11.42 (0.25C), 11.46 (0.25C), 11.59 (0.5C), 12.20 (0.75C), 12.27 (0.25C), 17.06 (0.5C), 17.11 (0.25C), 17.13 (0.25C), 17.77 (0.25C), 17.89 (0.25C), 17.95 (0.25C), 17.96 (0.25C), 27.10 (0.25C), 27.16 (0.25C), 27.25 (0.25C), 27.28 (0.25C), 27.53 (0.5C), 27.56 (0.25C), 27.60 (0.25C), 33.54 (0.25C), 33.58 (0.25C), 34.44 (0.25C), 34.45 (0.25C), 37.30 (0.25C), 37.39 (0.25C), 37.78 (0.5C), 48.72 (0.5C), 51.52 (0.25C), 51.55 (0.25C), 52.13 (0.25C), 52.16 (0.25C), 52.59 (0.25C), 52.60 (0.25C), 126.21, 127.23 (0.5C), 127.53 (0.5C), 128.08 (0.5C), 128.09 (0.5C), 128.62 (0.5C), 128.93 (0.5C), 137.69 (0.5C), 138.29 (0.5C), 177.41 (0.25C), 177.43 (0.25C), 177.67 (0.5C) ppm. Diastereomers resulting from the asymmetric carbon atoms at positions 2 and 2' and the asymmetric nitrogen atom of which inversion is difficult due to steric hindrance were present at a ratio of ~50:50 in the $^1$H- and $^{13}$C-NMR samples in CDCl$_3$.

GC-MS (EI, 70 eV): 41, 57, 77, 91, 106, 120 (base peak), 134, 148, 163, 190, 204, 218, 232, 246, 261 (M$^+$).

Comparative Example 3: Preparation of (2RS,2'RS)-N-benzyl-2-methyl-N-(2'-methylbutyl)butanamide: (2RS,2'RS)-(6) (a ~25:25:25:25 mixture of (2R,2'R)-(6), (2R,2'S)-(6), (2S,2'R)-(6), and (2S,2'S)-(6))

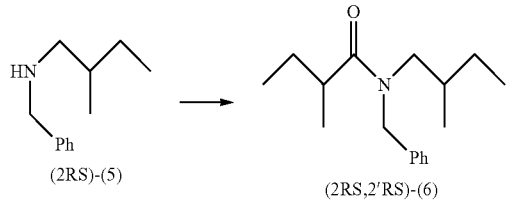 [SMILES: CCC(C)CNCc1ccccc1 ; CCC(C)CN(Cc1ccccc1)C(=O)C(C)CC]

To a mixture of 10.3 g of (±)-benzyl-2-methylbutylamine, 18.0 g of triethylamine, and 60 ml of tetrahydrofuran was added 10.0 g of butyryl chloride at room temperature in a nitrogen atmosphere with stirring. The reaction mixture was stirred at room temperature for 30 hours, poured into dilute hydrochloric acid, and then subjected to extraction with ethyl acetate. The organic layer was subjected to aftertreatment, i.e., washing, drying, and concentration, and the concentrate was purified by silica gel column chromatography to obtain 19.83 g of the target compound (94.5% GC, quantitative yield).

(2RS,2'RS)-N-Benzyl-2-methyl-N-(2'-methylbutyl)butanamide: (2RS,2'RS)-(6) (a ~25: 25:25:25 mixture of (2R, 2'R)-(6), (2R,2'S)-(6), (2S,2'R)-(6), and (2S,2'S)-(6)): C$_{17}$H$_{27}$NO Colorless liquid.

Various spectra of this compound were the same as those of (2RS,2'S)-N-benzyl-2-methyl-N-(2'-methylbutyl)butanamide: (2RS,2'S)-(6) determined in Comparative Example 2.

Comparative Example 4: Attempt 1 of preparation of (2RS,2'RS)-2-methyl-N-(2'- methylbutyl)butanamide: (2RS,2'RS)-(1) (a—25:25:25:25 mixture of (2R,2'R)-(1), (2R,2'S)-(1), (2S,2'R)-(1), and (2S,2'S)-(1))

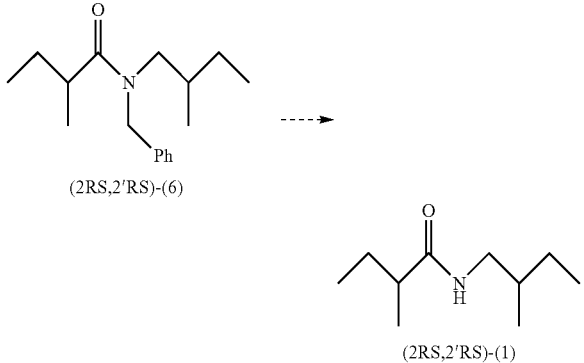

A mixture of 4.03 g of (2RS,2'RS)-N-benzyl-2-methyl-N-(2'-methylbutyl)butanamide: (2RS,2'RS)-(6) obtained in Comparative Example 3, 0.25 g of Pd-C (palladium on active carbon), 0.25 g of Pd(OH)2-C (palladium hydroxide on active carbon), and 20 ml of methanol was vigorously stirred in an autoclave under a hydrogen pressure of 0.47 to 0.52 MPa at room temperature for 3 hours, at 60° C. for 5.5 hours, and further at 80° C. for 5.5 hours. The reaction mixture had a conversion of 6.8% as determined by GC.

Similar hydrogenolysis reactions were carried out under various conditions such as catalysts, solvents, and additives including acids, but all the conditions resulted in slow rates of reaction and failed to achieve practical reaction rates.

Comparative Example 5: Attempt 2 of preparation of (2RS,2'RS)2-methyl-N-(2'-methylbutyl)butanamide: (2RS,2'RS)-(1) (a~25:25:25:25 mixture of (2R,2'R)-(1), (2R,2'S)-(1), (2S,2'R)-(1), and (2S,2'S)-(1))

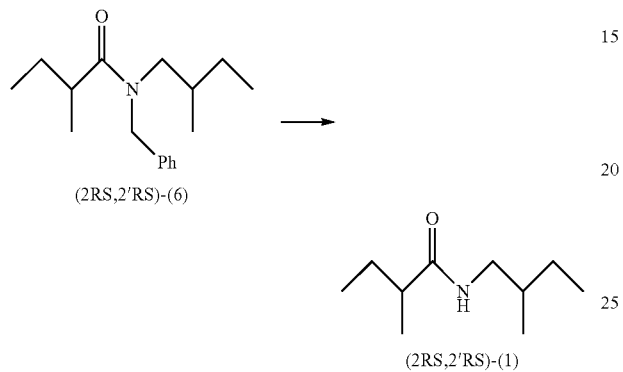

(2RS,2'RS)-(6)

(2RS,2'RS)-(1)

To a mixture of 0.88 g of (2RS,2'RS)-N-benzyl-2-methyl-N-(2'-methylbutyl)butanamide: (2RS,2'RS)-(6) obtained in Comparative Example 3 and 20 ml of ethyl acetate was added 0.55 g of N-bromo succinimide (NBS) and then 0.10 g of azobisisobutyronitrile (AIBN) in a nitrogen atmosphere with stirring at room temperature. The reaction mixture was heated under reflux for 10 hours and then stirred at room temperature for 16 hours. Water was added to the reaction mixture, and the resulting organic layer was subjected to aftertreatment, i.e., washing, drying, and concentration, and the concentrate was purified by silica gel column chromatography to obtain 0.20 g of the target compound as colorless liquid (94.0% GC, yield 36%).

Various spectra of (2RS,2'RS)-(1) thus prepared were the same as those of (2S,2'RS)-2-methylbutyl-α-phenylethylamine: (2S,2'RS)-(1) determined in Example 6.

The invention claimed is:
1. A process for preparing 2-methyl-N-(2'-methylbutyl)butanamide of the following formula (1):

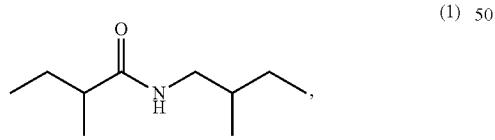

(1)

the process comprising:
subjecting an α-arylethyl-2-methylbutylamine compound of the following general formula (2):

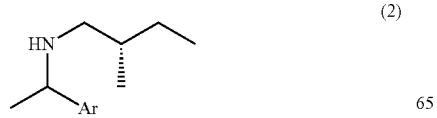

(2)

wherein Ar represents a substituted or unsubstituted aryl group having 6 to 20 carbon atoms, to N-2-methylbutyrylation to form an N-α-arylethyl-2-methyl-N-(2'-methylbutyl)butanamide compound of the following general formula (3):

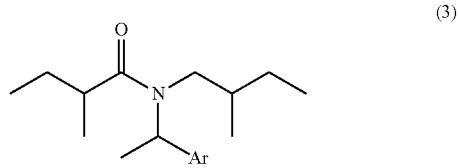

(3)

wherein Ar is as defined above, and
removing the α-arylethyl group of the resulting compound (3) to form 2-methyl-N-(2'-methylbutyl)butanamide (1).

2. The process for preparing 2-methyl-N-(2'-methylbutyl)butanamide (1) according to claim 1, the process further comprising
subjecting an α-arylethylamine compound of the following general formula (4):

(4)

wherein Ar represents a substituted or unsubstituted aryl group having 6 to 20 carbon atoms to N-2-methylbutylation to form the α-arylethyl-2-methylbutylamine compound (2).

3. The process for preparing 2-methyl-N-(2'-methylbutyl)butanamide (1) according to claim 1,
wherein the N-α-arylethyl-2-methyl-N-(2'-methylbutyl)butanamide compound (3) is a (2S)-N-α-arylethyl-2-methyl-N-(2'-methylbutyl)butanamide compound of the following general formula (2S)-(3):

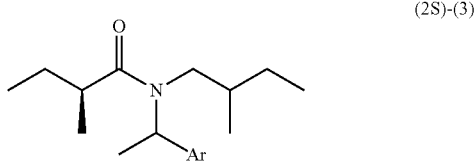

(2S)-(3)

wherein the wedged bond represents an absolute configuration, and Ar represents a substituted or unsubstituted aryl group having 6 to 20 carbon atoms and
wherein the 2-methyl-N-(2'-methylbutyl)butanamide (1) is (2S)-2-methyl-N-(2'-methylbutyl)butanamide of the following general formula (2S)-(1):

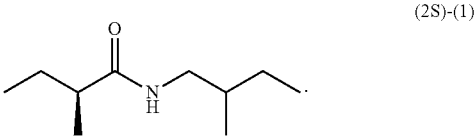

(2S)-(1)

4. The process for preparing 2-methyl-N-(2'-methylbutyl)butanamide (1) according to claim 2, wherein the α-arylethyl-2-methylbutylamine compound (2) is a (2S)-α-arylethyl-2-methylbutylamine compound of the following general formula (2S)-(2):

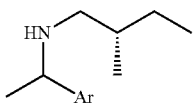
(2S)-(2)

wherein Ar represents a substituted or unsubstituted aryl group having 6 to 20 carbon atoms, wherein the N-α-arylethyl-2-methyl-N-(2'-methylbutyl)butanamide compound (3) is a (2'S)-N-α-arylethyl-2-methyl-N-(2'-methylbutyl)butanamide compound of the following general formula (2'S)-(3):

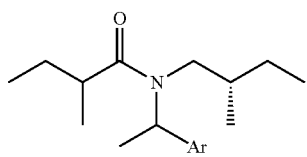
(2'S)-(3)

wherein Ar represents a substituted or unsubstituted aryl group having 6 to 20 carbon atoms, and wherein 2-methyl-N-(2'-methylbutyl)butanamide (1) is (2'S)-2-methyl-N-(2'-methylbutyl)butanamide of the following formula (2'S)-(1):

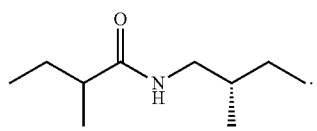
(2'S)-(1)

5. The process for preparing 2-methyl-N-(2'-methylbutyl)butanamide (1) according to claim 2, wherein the α-arylethyl-2-methylbutylamine compound (2) is a (2S)-α-arylethyl-2-methylbutylamine compound of the following general formula (2S)-(2):

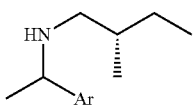
(2S)-(2)

wherein the wedged bond represents an absolute configuration, and Ar represents a substituted or unsubstituted aryl group having 6 to 20 carbon atoms, wherein the N-α-arylethyl-2-methyl-N-(2'-methylbutyl)butanamide compound (3) is a (2S,2'S)-N-α-arylethyl-2-methyl-N-(2'-methylbutyl)butanamide compound of the following general formula (2S,2'S)-(3):

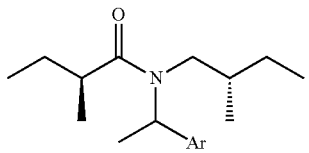
(2S,2'S)-(3)

wherein Ar represents a substituted or unsubstituted aryl group having 6 to 20 carbon atoms, and wherein 2-methyl-N-(2'-methylbutyl)butanamide (1) is (2S,2'S)-2-methyl-N-(2'-methylbutyl)butanamide of the following formula (2S,2' S)-(1):

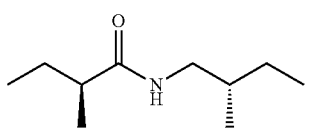
(2S,2'S)-(1)

6. The process for preparing 2-methyl-N-(2'-methylbutyl)butanamide (1) according to claim 1, the process further comprising, prior to the N-2-methylbutyrylation, isolating a mixture of diastereomers of an α-arylethylamine compound of the following general formulae (2R*,αR*)-(2) and (2S*,αR*)-(2):

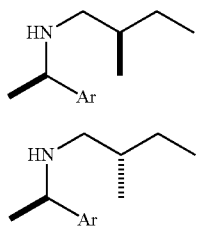
(2R*,αR*)-(2)

(2S*,αR*)-(2)

wherein the hashed bond and the bold bonds represent a relative configuration, and Ar represents a substituted or unsubstituted aryl group having 6 to 20 carbon atoms, from the α-arylethyl-2-methylbutylamine compound (2), and subjecting at least one of the α-arylethylamine compounds (2R*,αR*)-(2) and (2S*,αR*)-(2) isolated from the mixture of diastereomers to the N-2-methylbutyrylation and the removal of the α-arylethyl group.

7. The process for preparing 2-methyl-N-(2'-methylbutyl)butanamide (1) according to claim 3, wherein the α-arylethyl-2-methylbutylamine compound (2) is a (2S)-α-arylethyl-2-methylbutylamine compound of the following general formula (2S)-(2):

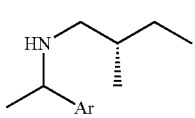
(2S)-(2)

wherein the wedged bond represents an absolute configuration, and Ar represents a substituted or unsubstituted aryl group having 6 to 20 carbon atoms, wherein the N-α-arylethyl-2-methyl-N-(2'-methylbutyl)butanamide compound (3) is a (2S,2'S)-N-α-arylethyl- 2-methyl-N-(2'-methylbutyl)butanamide compound of the following general formula (2S,2'S)-(3):

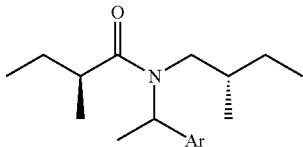

(2S,2'S)-(3)

wherein Ar represents a substituted or unsubstituted aryl group having 6 to 20 carbon atoms, and wherein 2-methyl-N-(2'-methylbutyl)butanamide (1) is (2S,2'S)-2-methyl-N-(2'-methylbutyl)butanamide of the following formula (2S,2'S)-(1):

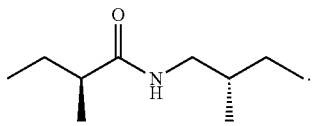

(2S,2'S)-(1)

8. The process for preparing 2-methyl-N-(2'-methylbutyl) butanamide (1) according to claim 4, wherein the α-arylethyl-2-methylbutylamine compound (2) is a (2S)-α-arylethyl-2-methylbutylamine compound of the following general formula (2S)-(2):

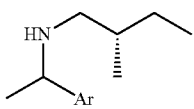

(2S)-(2)

wherein the wedged bond represents an absolute configuration, and Ar represents a substituted or unsubstituted aryl group having 6 to 20 carbon atoms, wherein the N-α-arylethyl-2-methyl-N-(2'-methylbutyl) butanamide compound (3) is a (2S,2'S)-N-α-arylethyl-2-methyl-N-(2'-methylbutyl)butanamide compound of the following general formula (2S,2'S)-(3):

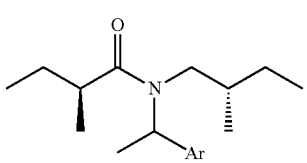

(2S,2'S)-(3)

wherein Ar represents a substituted or unsubstituted aryl group having 6 to 20 carbon atoms, and wherein 2-methyl-N-(2'-methylbutyl)butanamide (1) is (2S,2'S)-2-methyl-N-(2'-methylbutyl)butanamide of the following formula (2S,2'S)-(1):

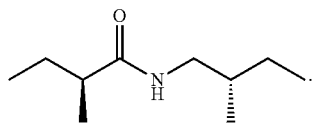

(2S,2'S)-(1)

9. The process for preparing 2-methyl-N-(2'-methylbutyl) butanamide (1) according to claim 2, the process further comprising, prior to the N-2-methyl-butyrylation, isolating a mixture of diastereomers of an α-arylethylamine compound of the following general formulae (2R*,αR*)-(2) and (2S*,αR*)-(2):

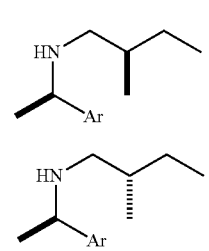

(2R*,αR*)-2

(2S,αR*)-(2)

wherein the hashed bond and the bold bonds represent a relative configuration, and Ar represents a substituted or unsubstituted aryl group having 6 to 20 carbon atoms from the α-arylethyl-2-methylbutylamine compound (2), and subjecting at least one of the α-arylethylamine compounds (2R*,αR*)-(2) and (2S*,αR*)-(2) isolated from the mixture of diastereomers to the N-2-methyl-butyrylation and the removal of the α-arylethyl group.

10. The process for preparing 2-methyl-N-(2'-methyl-butyl)butanamide (1) according to claim 3, the process further comprising, prior to the N-2-methyl-butyrylation, isolating a mixture of diastereomers of an α-arylethylamine compound of the following general formulae (2R*,αR*)-(2) and (2S*,αR*)-(2):

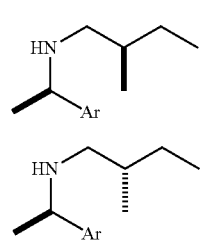

(2R*,αR*)-(2)

(2S*,αR*)-(2)

wherein the hashed bond and the bold bonds represent a relative configuration, and Ar represents a substituted or unsubstituted aryl group having 6 to 20 carbon atoms from the α-arylethyl-2-methylbutylamine compound (2), and subjecting at least one of the α-arylethylamine compounds (2R*,αR*)-(2) and (2S*,αR*)-(2) isolated from the mixture of diastereomers to the N-2-methyl-butyrylation and the removal of the α-arylethyl group.

11. The process for preparing 2-methyl-N-(2'-methyl-butyl)butanamide (1) according to claim 4, the process further comprising, prior to the N-2-methyl-butyrylation, isolating a mixture of diastereomers of an α-arylethylamine compound of the following general formulae (2R*,αR*)-(2) and (2S*,αR*)-(2):

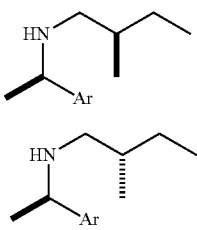 (2R*,αR*)-(2)

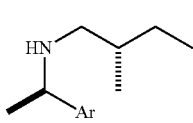 (2S,αR*)-(2)

wherein the hashed bond and the bold bonds represent a relative configuration, and Ar represents a substituted or unsubstituted aryl group having 6 to 20 carbon atoms from the α-arylethyl-2-methylbutylamine compound (2), and
subjecting at least one of the α-arylethylamine compounds (2R*,aR*)-(2) and (2S*,αR*)-(2) isolated from the mixture of diastereomers to the N-2-methylbutyrylation and the removal of the α-arylethyl group.

12. The process for preparing 2-methyl-N-(2'-methylbutyl)butanamide (1) according to claim 5,
the process further comprising, prior to the N-2-methylbutyrylation, isolating a mixture of diastereomers of an α-arylethylamine compound of the following general formulae (2R* ,αR*)-(2) and (2S*,αR*)-(2):

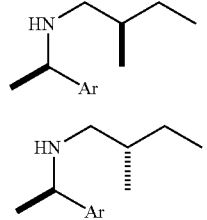 (2R*,αR*)-(2)

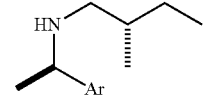 (2S,αR*)-(2)

wherein the hashed bond and the bold bonds represent a relative configuration, and Ar represents a substituted or unsubstituted aryl group having 6 to 20 carbon atoms from the α-arylethyl-2-methylbutylamine compound (2), and
subjecting at least one of the α-arylethylamine compounds (2R*,αR*)-(2) and (2S*,αR*)-(2) isolated from the mixture of diastereomers to the N-2-methylbutyrylation and the removal of the α-arylethyl group.

* * * * *

UNITED STATES PATENT AND TRADEMARK OFFICE
CERTIFICATE OF CORRECTION

PATENT NO. : 11,629,119 B2
APPLICATION NO. : 17/751974
DATED : April 18, 2023
INVENTOR(S) : Kinsho et al.

It is certified that error appears in the above-identified patent and that said Letters Patent is hereby corrected as shown below:

In the Specification

Column 15, Lines 10-15, Formula (2S)-(2): Please delete Formula (2S)-(2) and replace with the following:

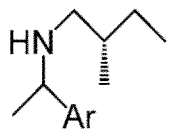

(2S)-(2)

Column 16, Line 50: Please correct "thereof An," to read --thereof. An--

Column 21, Line 59: Please correct "product]±[(mass" to read --product]÷[(mass--

Column 22, Line 67: Please correct "[α]D²²+67.5" to read --$[α]_D^{22}+67.5$--

Column 23, Line 6: Please correct "1.321.41" to read --1.32-1.41--

Column 24, Line 32: Please correct "(2S,2'S,'R)" to read --(2S,2'S,αR)--

Column 24, Lines 36-43, Formula (2S,2'S,αR)-(3a): Please delete Formula (2S,2'S,αR)-(3a) and replace with the following:

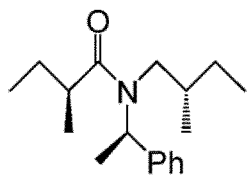

(2S,2'S,αR)-(3a)

Signed and Sealed this
Eighteenth Day of July, 2023

Katherine Kelly Vidal
*Director of the United States Patent and Trademark Office*

Column 24, Line 45: Please correct "[α]D$^{22}$+105.0" to read --[α]$_D^{22}$+105.0--

Column 26, Lines 1-2 : Please correct "(2S,2S)-(1)" to read --(2S,2'S)-(1)--

Column 26, Line 13: Please correct "[α]D$^{25}$+23.3" to read --[α]$_D^{25}$+23.3--

Column 27, Line 58: Please correct "[α]D$^{26}$+59.3" to read --[α]$_D^{26}$+59.3--

Column 28, Line 27: Please correct "[α]D$^{26}$+38.7" to read --[α]$_D^{26}$+38.7--

Column 28, Line 28: Please correct "[α]D$^{26}$+40.1" to read --[α]$_D^{26}$+40.1--

Column 28, Line 67: Please correct "[α]D$^{26}$+97.3 (c=1.0, CHC$_3$)" to read --[α]$_D^{26}$+97.3 (c=1.0, CHCl$_3$)--

Column 29, Line 4: Please correct "(600 MHz, CDC$_3$)" to read --(600 MHz, CDCl$_3$)--

Column 29, Line 7: Please correct "(-1H, m)" to read --(~1H, m)--

Column 29, Line 23: Please correct "(150 MHz, CDC13)" to read --(150 MHz, CDCl$_3$)--

Column 30, Line 16: Please correct "[α]D$^{23}$+19.5" to read --[α]$_D^{23}$+19.5--

Column 30, Line 23: Please correct "—7 Hz" to read --~7 Hz--

Column 30, Line 24: Please correct "—6.5 Hz" to read --~6.5 Hz--

Column 30, Line 24: Please correct "—6.0 Hz" to read --~6.0 Hz--

Column 30, Line 25: Please correct "—7 Hz" to read --~7 Hz--

Column 31, Line 50: Please correct "—7 Hz" to read --~7 Hz--

Column 31, Line 52: Please correct "—7 Hz" to read --~7 Hz--

Column 32, Lines 12-15, Formula (2RS,αRS)-(2a): Please delete Formula (2RS,αRS)-(2a) and replace with the following:

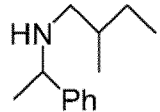

(2RS,αRS)-(2a)

Column 33, Line 6: Please correct "(2RS,2'RS,aRS)-(3a)" to read --(2RS,2'RS,αRS)-(3a)--

Column 34, Lines 3-4: Please remove the paragraph break between "used in" and "Example"

CERTIFICATE OF CORRECTION (continued)
U.S. Pat. No. 11,629,119 B2

Column 34, Line 18: Please correct "[α]D$^{26}$+4.83" to read --[α]$_D^{26}$+4.83--

Column 34, Line 21: Please correct "(2S,2'RS)" to read --(2S,2'RS)--

Column 35, Line 2: Please correct "[α]D$^{24}$-56.6" to read --[α]$_D^{24}$-56.6--

Column 35, Line 23: Please correct "(M$^{+)}$." to read --(M$^+$).--

Column 35, Line 60: Please correct "[α]D$^{26}$-61.4" to read --[α]$_D^{26}$-61.4--

Column 36, Line 22: Please correct "(2S,αS)" to read --(2S,αS)--

Column 36, Line 33: Please correct "[α]D$^{24}$-50.1" to read --[α]$_D^{24}$-50.1--

Column 37, Line 20: Please correct "$^{H-NMR}$(600 MHz, CDCl$_3$): ν=0.852" to read --$^1$H-NMR (600 MHz, CDCl$_3$): δ=0.852--

Column 37, Line 36: Please correct "(EU 70 eV)" to read --(EI, 70 eV)--

Column 37, Line 61: Please correct "C$_2$H$_5$OH:CH$_3$H$_5$OH:CH$_3$OH:" to read --C$_2$H$_5$OH:CH$_3$CN:CH$_3$OH:--

Column 38, Line 21: Please correct "[α]D$^{23}$+48.1" to read --[α]$_D^{23}$+48.1--

Column 38, Line 45: Please correct "[α]D$^{25}$+59.3" to read --[α]$_D^{25}$+59.3--

Column 38, Line 49: Please correct "(600 MHz, CDCl$_3$)" to read --$^1$H-NMR (600 MHz, CDCl$_3$)--

Column 39, Lines 61-62: Please remove the paragraph break between "obtained in" and "Examples"

Column 40, Line 47: Please correct "(-100% GC, yield 67%)" to read --(~100% GC, yield 67%)--

Column 40, Line 61: Please correct "[α]D$^{27}$+26.1" to read --[α]$_D^{27}$+26.1--

Column 41, Line 7: Please correct "J=-7.5 Hz" to read --J=~7.5 Hz--

Column 41, Line 19: Please correct "-50:50" to read --~50:50--

Column 41, Line 43: Please correct "[α]D$^{27}$-0.73" to read --[α]$_D^{27}$-0.73--

Column 41, Lines 53-54: Please remove the paragraph break between "J=~14.8" and "Hz),"

Column 42, Line 44: Please correct "a—25:25:25:25" to read --a ~25:25:25:25--

Column 42, Line 66: Please correct "Pd(OH)2-C" to read --Pd(OH)$_2$-C--

CERTIFICATE OF CORRECTION (continued)
U.S. Pat. No. 11,629,119 B2

Column 43, Line 11: Please correct "(25,2'R)-(1), and (25,2'S)-(1)" to read --(2S,2'R)-(1), and (2S,2'S)-(1)--

In the Claims

Column 43, Lines 61-65, Claim 1, General Formula (2): Please delete General Formula (2) and replace with the following:

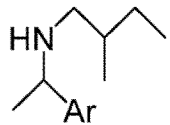

(2)

Column 46, Line 29, Claim 6: Please correct "(2S*, 60 R*)-(2)" to read --(2S*, αR*)-(2)--

Column 48, Line 16, Claim 9: Please correct "(2R*,αR*)-2)" to read --(2R*,αR*)-(2)--

Column 49, Line 18, Claim 11: Please correct "(2R*,aR*)-(2)" to read --(2R*,αR*)-(2)--